(12) United States Patent
March et al.

(10) Patent No.: US 10,328,116 B2
(45) Date of Patent: Jun. 25, 2019

(54) COMBINATIONS OF PROTEASOME INHIBITORS AND CYCLIC PEPTIDES

(71) Applicant: BIG DNA LTD, Roslin, Midlothian (GB)

(72) Inventors: John Bernard March, Midlothian (GB); Ewan McIntosh Clark, Midlothian (GB)

(73) Assignee: BIG DNA LTD, Roslin, Midlothian (GB)

( * ) Notice: Subject to any disclaimer, the term of this patent is extended or adjusted under 35 U.S.C. 154(b) by 0 days.

(21) Appl. No.: 15/523,188

(22) PCT Filed: Oct. 27, 2015

(86) PCT No.: PCT/GB2015/053215
§ 371 (c)(1),
(2) Date: Apr. 28, 2017

(87) PCT Pub. No.: WO2016/067010
PCT Pub. Date: May 6, 2016

(65) Prior Publication Data
US 2018/0021403 A1 Jan. 25, 2018

(30) Foreign Application Priority Data

Oct. 30, 2014 (GB) .................................. 1419311.4
Jan. 15, 2015 (GB) .................................. 1500681.0
Apr. 20, 2015 (GB) .................................. 1506673.1

(51) Int. Cl.
| | | |
|---|---|---|
| *A61K 38/12* | (2006.01) | |
| *A61K 38/06* | (2006.01) | |
| *A61K 31/407* | (2006.01) | |
| *A61K 38/07* | (2006.01) | |
| *A61K 38/05* | (2006.01) | |
| *A61K 38/00* | (2006.01) | |
| *A61K 31/69* | (2006.01) | |
| *A61K 45/06* | (2006.01) | |
| *A61K 31/4015* | (2006.01) | |

(52) U.S. Cl.
CPC ............ *A61K 38/12* (2013.01); *A61K 31/407* (2013.01); *A61K 31/4015* (2013.01); *A61K 31/69* (2013.01); *A61K 38/005* (2013.01); *A61K 38/05* (2013.01); *A61K 38/06* (2013.01); *A61K 38/07* (2013.01); *A61K 45/06* (2013.01)

(58) Field of Classification Search
CPC ...... A61K 38/12; A61K 38/05; A61K 38/005; A61K 31/407; A61K 31/4015; A61K 45/06; A61K 38/06; A61K 31/69; A61K 38/07; A61K 2300/00
See application file for complete search history.

(56) References Cited

U.S. PATENT DOCUMENTS

2012/0308562 A1* 12/2012 Derynck .............. A61K 31/519
424/133.1

FOREIGN PATENT DOCUMENTS

| WO | WO 2008/087025 A2 | 7/2008 |
|---|---|---|
| WO | WO 2010/096627 A1 | 8/2010 |
| WO | WO 2011/038924 | 4/2011 |
| WO | WO 2011/079015 A1 | 6/2011 |
| WO | WO 2012/007137 | 1/2012 |
| WO | WO 2012/167870 A1 | 12/2012 |
| WO | WO 2013/170066 A1 | 11/2013 |
| WO | WO 2014/084378 | 6/2014 |

OTHER PUBLICATIONS

Cilengitide, from https://www.medchemexpress.com/Cilengitide.html, p. 1, accessed Nov. 28, 2017.*
Cellular and Molecular Basis of Cancer, from http://www.merckmanuals.com/professional/print/hematology_and_oncology/overview_of . . . , pp. 1-5, accessed Nov. 7, 2012.*
Hait, Anticancer drug development: the grand challenges, Nature Reviews/Drug Disvovery, 2010, 9, pp. 253-254.*
Herter-Sprie et al, New cast for a new era: preclinical cancer drug development revisited, The Journal of Clinical Investigation, 2013, 123, pp. 3639-3645.*
Nieberler et al, Exploring the Role of RGD—Recognizing Integrins in Cancer, Cancers, 2017, 9, pp. 1-33.*
Milano et al, The proteasome: A worthwhile target for the treatment of solid tumours?, 2007, European Journal of Cancer, 2007, 43, pp. 1125-1133.*
Orlowski et al, Phase I Trial of the Proteasome Inhibitor PS-341 in Patients With Refractory Hematologic Malignancies, J Clin Oncol, 2002, 20, pp. 4420-4427.*
Chauhan et al, In Vitro and in Vivo Selective Antitumor Activity of a Novel Orally Bioavailable Proteasome Inhibitor MLN9708 against Multiple Myeloma Cells, Clin Cancer Res, 2011, 17, pp. 5311-5321.*
Ria et al, αvβ3 integrin engagement enhances cell invasiveness in human multiple myeloma, Haematologica, 2002, 87, pp. 836-845.*
Reardon et al, Cilengitide: A Prototypic Integrin Inhibitor for the Treatment of Glioblastoma and Other Malignancies, Genes & Cancer, 2011, 2, pp. 1159-1165.*
Bhandari, M.S. et al., "Clinical Trials in Metastatic Prostate Cancer—Has there been Real Progress in the Past Decade?", Euro. J. of Cancer, vol. 41, p. 941-953 (2005).
Kapoor, P. et al., "Bortezomib Combination Therapy in Multiple Myeloma", Seminars in Hematology., vol. 49, No. 3, p. 228-242 (2012).
Kisselev, A.F.et al., "Proteasome Inhibitors: An Expanding Army Attacking a Unique Target", Chemistry and Biology, vol. 19, No. 1, p. 99-115, (2012).
Patentscope English Translation of WO2014/084378.

* cited by examiner

Primary Examiner — Karlheinz R. Skowronek
Assistant Examiner — Li N Komatsu
(74) Attorney, Agent, or Firm — Morgan, Lewis & Bockius LLP

(57) ABSTRACT

The present invention relates to a combination comprising a proteasome inhibitor and a cyclic peptide that comprises an exposed Arg-Gly-Asp (RGD) moiety. In particular, the present invention relates to a combination comprising a proteasome inhibitor selected from the group consisting of: a boronate, an epoxyketone, a peptide aldehyde and a β-lactone protease inhibitor; and a cyclic peptide that comprises an exposed Arg-Gly-Asp (RGD) moiety. More particularly, the present invention relates to a combination comprising a proteasome inhibitor selected from the group consisting of: bortezomib, delanzomib, ixazomib, carfilzomib, oprozomib, MG132 and marizomib; and a cyclic peptide that comprises an exposed Arg-Gly-Asp (RGD) moiety.

23 Claims, 7 Drawing Sheets

COMBINATIONS OF PROTEASOME INHIBITORS AND CYCLIC PEPTIDES

CROSS-REFERENCE TO RELATED APPLICATIONS

This application is a US National Phase of International Patent Application No. PCT/GB2015/053215, filed Oct. 27, 2015, which claims priority to United Kingdom Patent Application No. 1419311.4, filed on Oct. 30, 2014, United Kingdom Patent Application No. 1500681.0, filed on Jan. 15, 2015 and United Kingdom Patent Application No. 1506673.1, filed on Apr. 20, 2015 the disclosures of which is incorporated herein in its entirety for all purposes.

FIELD OF THE INVENTION

The present invention relates to a combination comprising a proteasome inhibitor and a cyclic peptide that comprises an exposed Arg-Gly-Asp (RGD) moiety. In particular, the present invention relates to a combination comprising a proteasome inhibitor selected from the group consisting of: a boronate, an epoxyketone, a peptide aldehyde and a β-lactone protease inhibitor; and a cyclic peptide that comprises an exposed Arg-Gly-Asp (RGD) moiety. More particularly, the present invention relates to a combination comprising a proteasome inhibitor selected from the group consisting of: bortezomib, delanzomib, ixazomib, carfilzomib, oprozomib, MG132 and marizomib; and a cyclic peptide that comprises an exposed Arg-Gly-Asp (RGD) moiety.

The present invention relates to a combination that is useful as a medicament, for example in the treatment of hyper proliferative diseases, such as cancer.

The present invention also relates to a pharmaceutical composition comprising the combination and to kits comprising each component of the combination.

BACKGROUND OF THE INVENTION

Bortezomib (BTZ) is an anti-neoplastic agent for intravenous injection (IV) or subcutaneous (SC) use. The structure of bortezomib is:

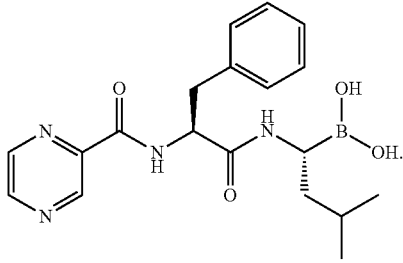 [SMILES: CC(C)C[C@H](NC(=O)[C@H](Cc1ccccc1)NC(=O)c1cnccn1)B(O)O]

Bortezomib is a reversible inhibitor of the chymotrypsin-like activity of the 26S proteasome in mammalian cells. The 26S proteasome is a large protein complex that degrades ubiquitinated proteins. The ubiquitin-proteasome pathway plays an essential role in regulating the intracellular concentration of specific proteins, thereby maintaining homeostasis within cells. Inhibition of the 26S proteasome prevents this targeted proteolysis which can affect multiple signalling cascades within the cell. This disruption of normal homeostatic mechanisms can lead to cell death. Experiments have demonstrated that bortezomib is cytotoxic to a variety of cancer cell types in vitro. Bortezomib causes a delay in tumour growth in vivo in nonclinical tumour models, including multiple myeloma.

Data from in vitro, ex-vivo, and animal models with bortezomib suggest that it increases osteoblast differentiation and activity and inhibits osteoclast function. These effects have been observed in patients with multiple myeloma affected by an advanced osteolytic disease and treated with bortezomib.

Delanzomib (DLZ), ([(1R)-1-[[(2S,3R)-3-Hydroxy-2-[[(6-phenylpyridin-2-yl)carbonyl]amino]-1-oxobutyl]amino]-3-methylbutyl]boronic acid), is an anti-neoplastic agent for intravenous injection (IV), oral or subcutaneous (SC) use. The structure of delanzomib is:

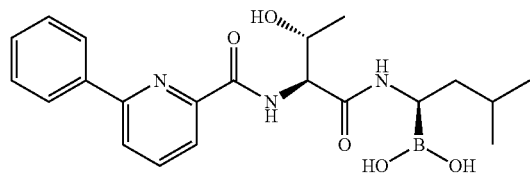

Delanzomib is also a reversible inhibitor of the chymotrypsin-like activity of the 26S proteasome in mammalian cells. Experiments have demonstrated that delanzomib is cytotoxic to multiple myeloma cell lines in vitro (Piva et al. Blood 2008; 111:2765-75, Dorsey et al., J. Med Chem 2008; 51:1068-72). Delanzomib causes a reduction in tumour growth in vivo in nonclinical tumour models, including multiple myeloma (Sanchez et al., Br. J. Haematol 2010; 148:569-81).

Ixazomib (IXZ) is an anti-neoplastic agent for intravenous injection (IV), oral or subcutaneous use. Ixazomib is formulated with citric acid for clinical use: the citrate hydrolyses immediately on contact with plasma or aqueous solutions (Kupperman et al., Cancer Res. 2010; 70:1970-80). The final formulation is termed ixazomib citrate, originally designated 'MLN9708', which contains the active drug component 'MLN2238' (ixazomib) and a citric acid moiety.

The structure of Ixazomib (MLN2238) ([(1R)-1-[[2-[(2,5-dichlorobenzoyl)amino]acetyl]amino]-3-methyl-butyl] boronic acid) is provided below:

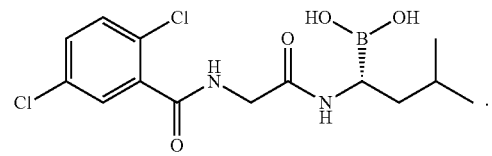 [SMILES: CC(C)C[C@H](NC(=O)CNC(=O)c1cc(Cl)ccc1Cl)B(O)O]

The structure of Ixazomib citrate (MLN9708) (2,2'-{2-[(1R)-1-{[N-(2,5-Dichlorobenzoyl)glycyl]amino}-3-methylbutyl]-5-oxo-1,3,2-dioxaborolane-4,4-diyl}diacetic acid) is provided below:

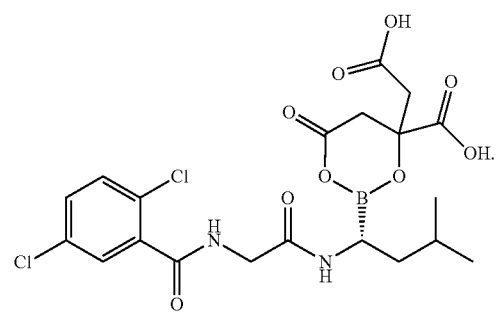 [SMILES: CC(C)C[C@H](NC(=O)CNC(=O)c1cc(Cl)ccc1Cl)B1OC(=O)CC(CC(=O)O)(C(=O)O)O1]

Ixazomib is also a reversible inhibitor of the chymotrypsin-like activity of the 26S proteasome in mammalian cells.

Kupperman and co-workers (Kupperman et al., Cancer Res. 2010; 70:1970-80) describe the physiochemical, phamocokinetic, pharmacodynamic, antitumoral activity and interactions of ixazomib with the proteasome compared with bortezomib. Both bortezomib and ixazomib bind preferentially to the β5 site of the 20S proteasome, also binding to the β2 and β1 sites at higher concentrations. Although the affinity for the active sites in the proteasome is approximately equal for ixazomib and bortezomib, ixazomib was found to remain bound to the proteasome for a shorter time period. The proteasome dissociation half-life of ixazomib is approximately 18 minutes, whereas the dissociation half-life of bortezomib is approximately 110 minutes, i.e. ixazomib is released approximately 6-fold faster than bortezomib. Ixazomib is cytotoxic to a variety of cancer cell lines in vitro including melanoma, lung cancer and colorectal cancer cell lines. Ixazomib also exhibited antitumoral activity in vivo in several preclinical models. In CWR22 human prostate cancer xenografts, both bortezomib and ixazomib showed effective anti-tumoral activity at their maximum tolerated dose (MTD). Ixazomib proved more effective than bortezomib at half the MTD. In WSU-DLCL2 lymphoma xenograft model, ixazomib showed significant anti-tumoral activity whereas bortezomib was ineffective at its MTD. Similarly, in Oci-Ly7-Luc model, representing disseminated lymphoma, animals treated with ixazomib exhibited an improved antitumoral effect compared with bortezomib. Ixazomib was also found to have oral bioavailability, meaning that oral dosing may be an option for treatments including ixazomib (Kupperman et al., Cancer Res. 2010; 70:1970-80). Lee and co-workers extended this analysis to include several further lymphoma models, both xenograft based lymphoma models (OCI-Ly10 and PHTX22L), and genetically-engineered mouse model iMyc$^{cα}$/Bcl-X$_L$, designed to be more representative of the clinical progression of human cancers. In each case, MTD level treatment with ixazomib was as least as effective as MTD-level treatment with bortezomib. In the case of PHTX22L xenografts only ixazomib was found to exhibit an anti-tumoral effect. Ixazomib was also effective in the alleviation of osteolytic bone disease in the DP54-Luc model (Lee et al., Clin. Cancer Res. 2011; 17:7313-23). It should be noted that, due to the higher MTD exhibited by ixazomib in the animal models, ixazomib was delivered at more than tenfold higher concentrations than bortezomib in the studies of Kupperman and Lee et al., therefore the improvements seen may be related to the higher doses delivered rather than the chemical properties of ixazomib. Nevertheless, reduced toxicity compared with bortezomib is an important feature of ixazomib, defining its potential clinical applicability (meaning that increased doses of ixazomib compared with bortezomib are clinically feasible).

When assessed in clinical trials, ixazomib citrate has been found to be well tolerated by both oral and intravenous routes, with MTD values which are generally greater than those exhibited by bortezomib. Ixazomib citrate has been trialled for the intravenous treatment of various solid tumours and non-Hodgkins lymphoma as well as oral treatment of multiple myeloma (reviewed in Allegra et al., Leukemia Research 2014; 38: 1-9). Phase III clinical trails are planned for evaluation of ixazomib citrate in combination with Revlimid® (lenalidomide) and dexamethasone for treatment of myeloma or systemic light chain amyloidosis, delivered orally in each case (clintrials.gov identifiers NCT01564537, NCT01659658, NCT01850524 and NCT0218141).

Carfilzomib (CFZ) has the structure:

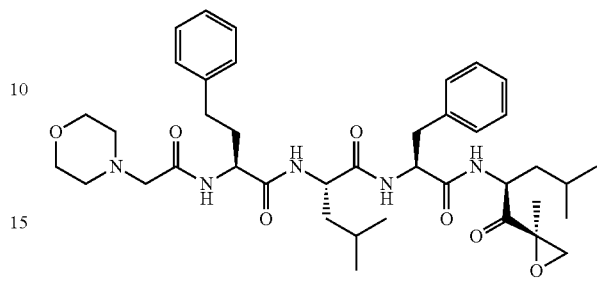

Carfilzomib causes stronger inhibition of the chymotrypsin-like activity of the proteasome in blood of patients than bortezomib—88% at the highest dose used in the phase I trial, where the maximal tolerated dose has not been reached (O'Conner et al, 2009 Clin. Cancer Res. 15, 7085-7091). In phase II trials, carfilzomib has achieved 24% partial response rate in a heavily pretreated patient population, a median of five prior lines of multidrug therapy (Kisselev et al, Chemistry & Biology 19, 27 Jan. 2012, 99-115). Incidents of peripheral neuropathies are greatly reduced compared to bortezomib (Molineaux, S. M. (2012), Clin. Cancer Res. 18, 15-20).

Oprozomib (OPZ) has the structure:

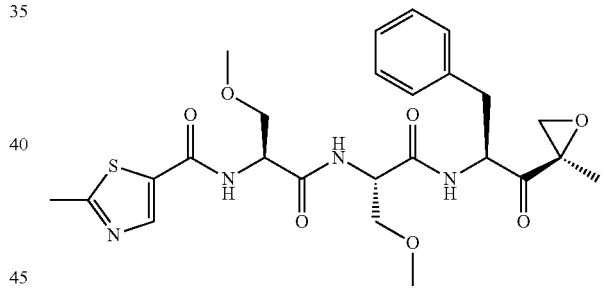

Oprozomib is an orally available analogue of carfilzomib (Zhou, H. J., et al. (2009). J. Med. Chem. 52, 3028-3038).

MG-132 has the structure:

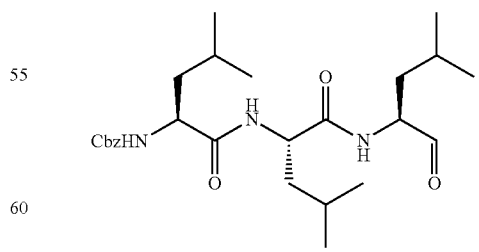

MG-132 is a rapidly reversible, potent inhibitor that blocks proteasomes by forming a hemiacetal with the hydroxyl of the active site threonines (Kisselev et al, Chemistry & Biology 19, 27 Jan. 2012, 99-115).

Marizomib has the structure:

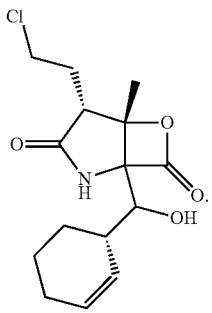 [SMILES: C[C@@]12OC(=O)C1(C(O)[C@@H]1C=CCCC1)NC(=O)[C@@H]2CCCl]

Marizomib is derived from a marine microorganism, *Salinispora tropica* (Chauhan et al, Cancer Cell 8, 407-419). Marizomib inactivates proteasomes by esterifying the catalytic threonine hydroxyl. The opening of the β-lactone ring is followed by formation of a tetrahydrofuran ring as the result of nucleophilic displacement of the chloride atom of the inhibitor (Groll et al, J. Am. Chem. Soc. 128, 5136-5141). All β-lactone adducts are slowly hydrolyzed by water, resulting in reactivation of the proteasome (Dick et al, J. Biol. Chem. 272, 182-188). Marizomib is the most potent of all proteasome inhibitors presently undergoing clinical trials. It produces stronger (up to 100%) and longer-lasting inhibition of the chymotrypsin-like sites and also targets the trypsin-like and the caspase-like sites (Potts et al, Curr. Cancer Drug Targets 11, 254-284).

Peptides containing an exposed RGD (arginine-glycine-aspartic acid) amino acid sequence are known to bind to integrins and have been heavily studied for targeted drug delivery (for review see Temming et al Drug Resistance Updates 8 (2005) 381-402). RGD-containing peptides have also been directly trialled as anti-cancer agents, on account of their binding to alphaV beta3 integrins which are overexpressed on certain cancers and in particular on tumour vasculator. One such example is Cilengitide or EMD121974, a 5 amino acid circularised peptide containing the RGD sequence which has been tested in clinical trials for melanoma, glioblastoma and prostate cancer. Although the three amino acid RGD motif is itself immutable, the specificity and avidity of targeting can be altered by changing the number and composition of the flanking amino acid sequences. Maintaining the core RGD sequence within a circularised structure containing a D-amino acid exhibits increased stability and binding avidity for alpha integrins.

Cilengitide has been the subject of at least 38 clinical trials (14 phase I, 5 phase I/II, 17 phase II and 2 phase III) in the US and Europe in which the drug has been trialled in patients with non-small cell lung cancer, gliomas, glioblastoma, brain tumours, breast tumours, metastatic squamous cell carcinoma of the head and neck, prostate cancer, leukemia, melanoma, lymphoma and advanced solid tumours, Kaposi's sarcoma. In terms of combination therapies, cilengitide has been tested in combination with Bevacizumab, Procarbazine, Radiochemotherapy (standard radiotherapy and cisplatin and vinorelbine based chemotherapy), Temozolomide, Corticosteriods, Radiation Therapy, Cediranib maleate, Paclitaxel, Cetuximab, 5-fluorouracil (5-FU), Sunitinib malate, Venorelbine and Gemcitabine. However, none of these combinations has yet been approved by the US or European agencies.

We have found that a combination of a proteasome inhibitor with a cyclic peptide that comprises an exposed Arg-Gly-Asp (RGD) moiety yields a synergistic therapeutic effect relative to the sum of each of the individual components.

SUMMARY OF THE INVENTION

In one aspect of the present invention, there is provided a combination comprising: (i) a proteasome inhibitor and pharmaceutically acceptable salts thereof; and (ii) a cyclic peptide, wherein the cyclic peptide comprises an exposed Arg-Gly-Asp (RGD) moiety.

In another aspect of the present invention, there is provided a combination comprising: (i) a proteasome inhibitor and pharmaceutically acceptable salts thereof; and (ii) a cyclic peptide, wherein the cyclic peptide comprises an exposed Arg-Gly-Asp (RGD) moiety for use as a medicament.

In another aspect of the present invention, there is provided a combination comprising: (i) a proteasome inhibitor and pharmaceutically acceptable salts thereof; and (ii) a cyclic peptide, wherein the cyclic peptide comprises an exposed Arg-Gly-Asp (RGD) moiety for use in the treatment of an oncology disorder, for example, a hyper proliferative diseases, such as cancer.

In another aspect of the present invention, there is provided a method of treating an oncology disorder, for example, a hyper proliferative diseases, such as cancer, comprising administering to a subject in need thereof a combination comprising: (i) a proteasome inhibitor and pharmaceutically acceptable salts thereof; and (ii) a cyclic peptide, wherein the cyclic peptide comprises an exposed Arg-Gly-Asp (RGD) moiety.

In another aspect of the present invention, there is provided a pharmaceutical composition comprising the combination of the invention and a pharmaceutically acceptable excipient.

In another aspect of the present invention, there is provided a kit comprising as separate components: (i) a proteasome inhibitor and pharmaceutically acceptable salts thereof; and (ii) a cyclic peptide, wherein the cyclic peptide comprises an exposed Arg-Gly-Asp (RGD) moiety.

In another aspect of the present invention there is provided a use of a cyclic peptide, wherein the cyclic peptide comprises an exposed Arg-Gly-Asp (RGD) moiety, for improving the therapeutic activity of a proteasome inhibitor and pharmaceutically acceptable salts thereof.

These and other embodiments are disclosed or are apparent from and encompassed by the Detailed Description.

DESCRIPTION OF THE FIGURES

Embodiments of the invention are further described hereinafter with reference to the accompanying drawings, in which.

DETAILED DESCRIPTION OF THE INVENTION

Figure 1:
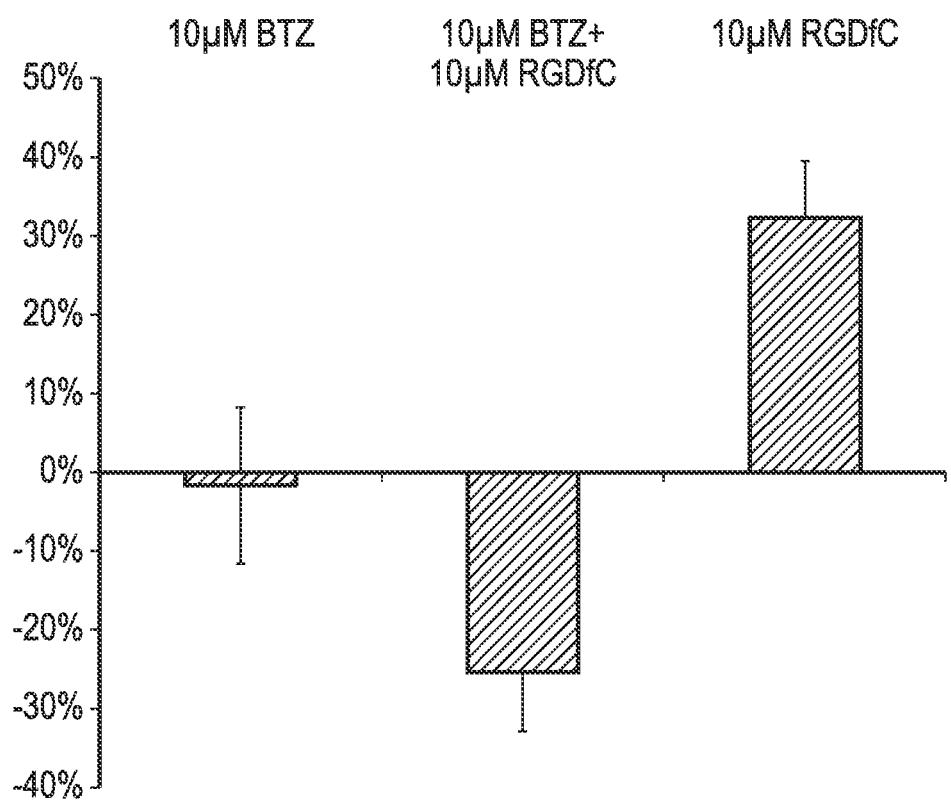
FIG. 1: Enhancement of proteasome inhibitor bortezomib by cysteine-containing cyclic RGD peptide. Histogram showing the % relative cell growth values compared to untreated HEK293 cells when treated with 10 µM BTZ, 10 µM BTZ combined with 10 µM RGDfC (Arginine-Glycine-Aspartic Acid-D-Phenylalanine-Cysteine) peptide or 10 µM RGDfC (Arginine-Glycine-Aspartic Acid-D-Phenylalanine-Cysteine) peptide without BTZ. Results are shown ±standard error of mean for the five experimental replicates included in the analysis. Control cell growth is assigned a relative cell growth value of 100% and all cell growth values are calculated relative to this figure.

The following embodiments apply equally to any of the above aspects of the present invention.

Proteasome Inhibitor:

In an embodiment, the proteasome inhibitor is a boronate compound.

In an embodiment, the proteasome inhibitor is an epoxyketone compound.

In an embodiment, the proteasome inhibitor is a peptide aldehyde compound.

In an embodiment, the proteasome inhibitor is a β-lactone protease inhibitor compound.

In an embodiment, the proteasome inhibitor is a boronate compound selected from the group consisting of: bortezomib, delanzomib and ixazomib. In an embodiment, the proteasome inhibitor is bortezomib. In an embodiment, the proteasome inhibitor is delanzomib. In an embodiment, the proteasome inhibitor is ixazomib.

In an embodiment, the proteasome inhibitor is an epoxyketone compound. In an embodiment, the proteasome inhibitor is carfilzomib. In an embodiment, the proteasome inhibitor is oprozomib.

In an embodiment, the proteasome inhibitor is a peptide aldehyde compound. In an embodiment, the proteasome inhibitor is MG132.

In an embodiment, the proteasome inhibitor is a β-lactone protease inhibitor compound. In an embodiment, the proteasome inhibitor is marizomib.

Cyclic Peptide Component:

In an embodiment the cyclic peptide has the structure:

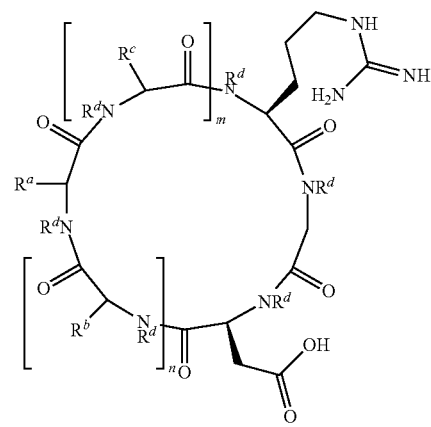

wherein:

$R^a$, $R^b$ and $R^c$ are amino acid side-chain residues;

$R^d$ are each independently selected from the group consisting of H, $C_1$ alkyl, $C_2$ alkyl and $C_3$ alkyl;

m is 0, 1 or 2;

n is 0, 1 or 2;

provided that the value of n+m is 0, 1 or 2.

In an embodiment the cyclic peptide has the structure:

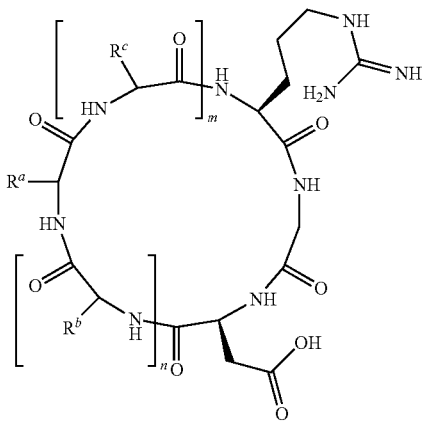

wherein:
R$^a$, R$^b$ and R$^c$ are amino acid side-chain residues;
m is 0, 1 or 2;
n is 0, 1 or 2;
provided that the value of n+m is 0, 1 or 2.

In an embodiment, R$^a$, R$^b$ and R$^c$ are amino acid side-chain residues of alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, selenocysteine or pyrrolysine.

In an embodiment, m is 0 and n is 0. In an alternative embodiment, m is 1 and n is 0. In an embodiment, m is 0 and n is 1. In an alternative embodiment, m is 1 and n is 1. In an alternative embodiment, m is 0 and n is 2. In an alternative embodiment, m is 2 and n is 0. Preferably, m is 0 and n is 1.

In an embodiment, R$^a$ is the amino acid side-chain residue of lysine.

In an embodiment, R$^b$ is the amino acid side-chain residue of phenylalanine.

In an embodiment, m is 0 and n is 1; R$^a$ is the amino acid side-chain residue of lysine; and R$^b$ is the amino acid side-chain residue of phenylalanine.

In an embodiment, each amine nitrogen of the amino acid of the amino acid residues of the cyclic peptide component can be independently mono-alkylated. In embodiments in which the amine nitrogen of one or more of the amino acids is mono-alkylated, the alkyl group is methyl or ethyl, preferably methyl. Thus, in an embodiment, at least one of the amino acid residues of cyclic peptide component is an N-methyl amino acid residue.

In an embodiment, the cyclic peptide component:

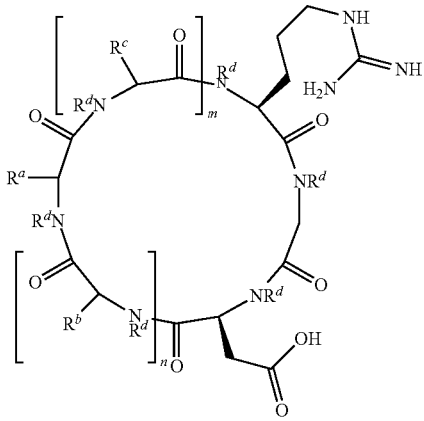

has a structure:

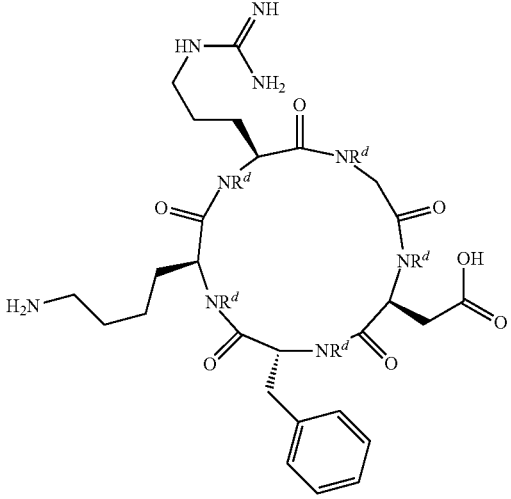

wherein R$^d$ are each independently selected from the group consisting of H, C$_1$ alkyl, C$_2$ alkyl and C$_3$ alkyl.

In an embodiment, the cyclic peptide component:

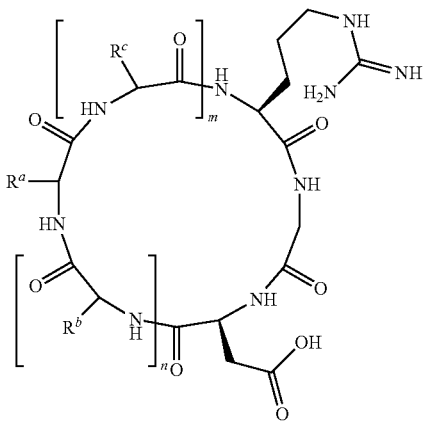

has a structure:

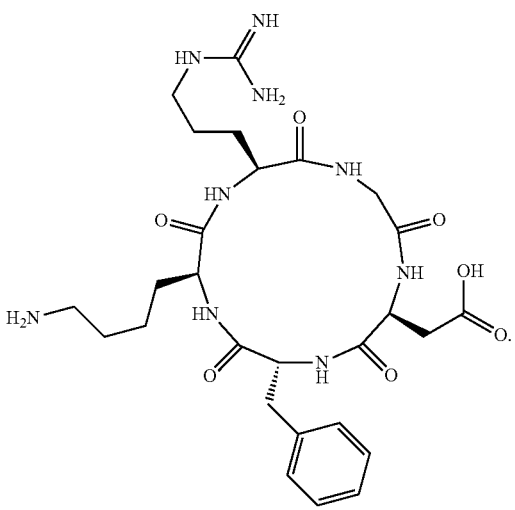 [SMILES: N=C(N)NCCC[C@@H]1NC(=O)[C@H](CCCCN)NC(=O)[C@@H](Cc2ccccc2)NC(=O)[C@H](CC(=O)O)NC(=O)CNC1=O]

In an embodiment, the cyclic peptide component is cilengitide, i.e. has the structure:

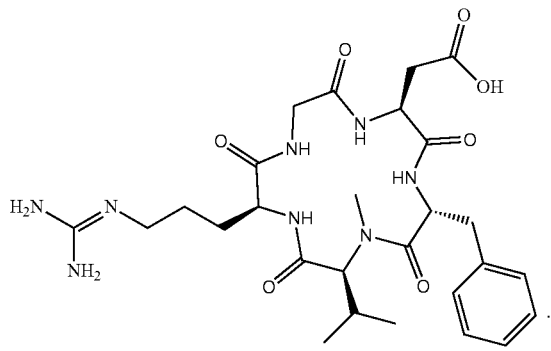 [SMILES: CC(C)[C@H]1C(=O)N[C@@H](CCCN=C(N)N)C(=O)NCC(=O)N[C@@H](CC(=O)O)C(=O)N[C@H](Cc2ccccc2)C(=O)N1C]

Combination of Proteasome Inhibitor and Cyclic Peptide Component

In an embodiment, the ratio of proteasome inhibitor to cyclic peptide component ranges from 1:20000 to 20000:1 w/w. In an embodiment, the ratio of proteasome inhibitor to cyclic peptide component ranges from 1:20000 to 1000:1 w/w. In an embodiment, the ratio of proteasome inhibitor to cyclic peptide component ranges from 1:20000 to 10:1 w/w. In an embodiment, the ratio of proteasome inhibitor to cyclic peptide component ranges from 1:10000 to 1000:1 w/w. In an embodiment, the ratio of proteasome inhibitor to cyclic peptide component ranges from 1:10000 to 10:1 w/w. In an embodiment, the ratio of proteasome inhibitor to cyclic peptide component ranges from 1:5000 to 1000:1 w/w. In an embodiment, the ratio of proteasome inhibitor to cyclic peptide component ranges from 1:5000 to 10:1 w/w. In an embodiment, the ratio of proteasome inhibitor to cyclic peptide component ranges from 1:2000 to 10:1 w/w. In an embodiment, the ratio of proteasome inhibitor to cyclic peptide component ranges from 1:1000 to 1000:1, preferably 1:100 to 1:100, more preferably 1:10 to 10:1 and still more preferably 1:1 w/w. In an embodiment, the ratio of proteasome inhibitor to cyclic peptide component ranges from 1:1000 to 1:1; 1:900 to 1:1; 1:800 to 1:1; 1:700 to 1:1; 1:600 to 1:1; or 1:500 to 1:1 w/w. In an embodiment, the ratio of proteasome inhibitor to cyclic peptide component ranges from 1:400 to 1:1; 1:450 to 1:1; 1:400 to 1:1; 1:350 to 1:1; 1:300 to 1:1; or 1:250 to 1:1 w/w. In an embodiment, the ratio of cyclic peptide:proteasome inhibitor is between 50:1 and 200:1, between 60:1 and 190:1, between 70:1 and 180:1 or between 70:1 and 170:1 w/w.

The invention provides a combination of a proteasome inhibitor and a cyclic peptide that comprises an exposed Arg-Gly-Asp (RGD) moiety that exhibits a synergistic therapeutic affect relative to each of the proteasome inhibitor and the cyclic peptide that comprises an exposed Arg-Gly-Asp (RGD) moiety. For example, the therapeutic effect of the combination of the invention is at least additive relative to each of the proteasome inhibitor and the cyclic peptide that comprises an exposed Arg-Gly-Asp (RGD) moiety. Preferably, the therapeutic effect of the combination of the invention is more than additive. For example, the synergistic effect is illustrated in the examples herein.

Diseases Treatable Using the Combination of the Invention

In an embodiment, the diseases treatable using a combination of the invention include a disorder selected from the group comprising: multiple myeloma and mantle cell lymphoma.

In an embodiment, the diseases treatable using a combination of the invention include a disorder selected from the group comprising: diffuse large B-cell lymphoma, prostate cancer, lung cancer, non-specific solid tumours and relapsed/refractory myeloma.

In an embodiment, the diseases treatable using a combination of the invention include an oncology disorder.

In an embodiment, the diseases treatable using a combination of the invention involve the treatment of a neoplasia.

In an embodiment, the diseases treatable using a combination of the invention include a disorder selected from the group consisting of: multiple myeloma (e.g. metastatic multiple myeloma); lung cancer; non-small cell lung cancer (e.g. metastatic non-small cell lung cancer, non-small cell lung carcinoma or metastatic non-small cell lung cancer); small cell lung carcinoma; solid tumours; lymphoma (e.g. lymphoplasmacytic lymphoma, diffuse large B-cell lymphoma, non-Hodgkin's lymphoma, follicular lymphoma or peripheral T-cell lymphoma); chronic lymphoid leukemia; T-Cell prolymphocytic leukemia; breast cancer (e.g. metastatic breast cancer); cervical cancer; colorectal cancer; colon cancer; melanoma; prostate cancer (e.g. hormone refractory prostate cancer); pancreatic cancer (e.g. metastatic pancreatic cancer); ovarian cancer; glioblastoma (e.g. glioblastoma multiforme); head squamous cell carcinoma; neck squamous cell carcinoma; amyloidosis (e.g. primary systemic amyloidosis); bone disorders; haematological malignancies; and graft-versus-host disease, or a combination thereof.

In an embodiment, the diseases treatable using a combination of the invention include a disorder selected from the group consisting of: Waldenström's Macroglobulinaemia, Smoldering Myeloma and monoclonal gammopathy of unknown significance (MGUS).

In an embodiment, the combination of the invention exhibits an improved cytotoxicity and/or improved anti-adherence (relative to the effect of the proteasome inhibitors and/or the effect of the cyclic peptide comprising an exposed Arg-Gly-Asp (RGD) moiety) to cells expressing RGD-sensitive integrins, such as $\alpha_v\beta_3$ or $\alpha_v\beta_5$ integrins. The expression of integrins is a factor in tumour angiogenesis and cell attachment.

In an embodiment, the combination of the invention exhibits an improved cytotoxicity and/or improved anti-adherence (relative to the effect of the proteasome inhibitors and/or the effect of the cyclic peptide comprising an exposed Arg-Gly-Asp (RGD) moiety) to cancers that are moderated by RGD-sensitive integrins, such as $\alpha_v\beta_3$ or $\alpha_v\beta_5$ integrins. The integrins may be expressed directly on the tumour cell or on cells which are not tumour cells, but which interact (e.g. by adherence or angiogenesis) with the tumour cells.

Definitions

The invention encompasses tautomeric forms of the compounds specifically disclosed, as well as geometrical and optical isomers where such are chemically possible. Thus, when the compounds specifically disclosed include an alkene double bond (for example, compounds having the moiety

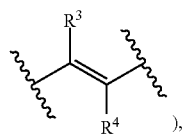

), the illustrated structures are intended to include both the E- and Z-geometrical isomers.

The term "amino acid side chain residue" includes a residue of both natural and synthetic amino acids. The class of natural amino acids includes both proteinogenic amino acids and also naturally occurring non-proteinogenic amino acids. These naturally occurring non-proteinogenic amino acids are those that may be found, for example, in the body or in food stuffs, but which do not participate in protein biosynthesis. There are twenty-two proteinogenic amino acids and of the twenty-two, only twenty are directly encoded by the universal genetic code. The remaining two, selenocysteine and pyrrolysine, are incorporated into proteins by unique synthetic mechanisms. The invention is intended to encompass the twenty universally encoded amino acids plus the remaining two mentioned above. The term "amino acid side chain residue" therefore includes the side chains of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, selenocysteine and pyrrolysine.

The side chains of the above amino acids can be in either the (R) or the (S) configuration. Thus, both L- and D-amino acids are within the scope of the present invention, though the D-amino acids are of course not naturally occurring.

As mentioned above, the term "amino acid side-chain residue" also includes non-proteinogenic amino acids such as amino acids which can be incorporated into proteins during translation (including pyrrolysine, ornithine and selenocysteine). The term "non-proteinogenic amino acid" also includes homologues of proteinogenic amino acids such as, but not limited to, homoarginine. The term "non-proteinogenic amino acid" also includes beta amino acids such as, but not limited to, beta alanine. The term "amino acid" also includes lactam analogues of natural amino acids such as, but not limited to, pyroglutamine.

A "non-proteinogenic amino acid" is an organic compound which is an amino acid, but is not among those encoded by the standard genetic code, or incorporated into proteins during translation. Non-proteinogenic amino acids, thus, include amino acids or analogues of amino acids other than the 20 proteinogenic amino acids and include, but are not limited to, the D-isostereomers of proteinogenic amino acids. Examples of non-proteinogenic amino acids include, but are not limited to: citrulline, homocitrulline, hydroxyproline, homoarginine, homoserine, homotyrosine, homoproline, ornithine, 4-amino-phenylalanine, sarcosine, biphenylalanine, homophenylalanine, 4-nitro-phenylalanine, 4-fluoro-phenylalanine, 2,3,4,5,6-pentafluoro-phenylalanine, norleucine, cyclohexylalanine, N-acetic acid, O-methyl serine (i.e., an amino acid side chain having the formula

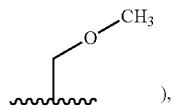 [SMILES: *COC]

acetylamino alanine (i.e., an amino acid side chain having the formula

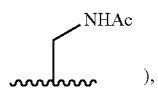

β-alanine, β-(acetylamino)alanine, β-aminoalanine, β-chloroalanine, α-aminoisobutyric acid, N-methyl-alanine, N-methyl-glycine, N-methyl-glutamic acid, tert-butylglycine, α-aminobutyric acid, α-aminoisobutyric acid, acedic acid, 2-aminoisobutyric acid, 2-aminoindane-2-carboxylic acid, selenomethionine, lanthionine, dehydroalanine, γ-amino butyric acid, naphthylalanine, aminohexanoic acid, phenylglycine, pipecolic acid, 2,3-diaminoproprionic acid, tetrahydroisoquinoline-3-carboxylic acid, tert-leucine, tert-butylalanine, cyclohexylglycine, diethylglycine, dipropylglycine and derivatives thereof wherein the amine nitrogen has been mono- or di-alkylated. Other examples of non-proteinogenic amino acids include para amino benzoic acid (PABA), 5-amino salicylic acid (5-ASA) and 4-amino salicylic acid (4-ASA).

The term "amino" includes a —NH$_2$ group.

The term "carrier" includes a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. In certain cases, an organic solvent such as ethanol, DMA (dimethylacetamide), NMP (N-methyl pyrrolidine), DMSO (dimethyl sulphoxide) etc. may be used alone or in combination with water as a carrier. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18$^{th}$ Edition.

The phrase "pharmaceutically acceptable" includes molecular entities and compositions that are generally regarded as safe. In particular, pharmaceutically acceptable carriers used in the practice of this invention are physiologically tolerable and do not typically produce an allergic or similar untoward reaction (for example, gastric upset, dizziness and the like) when administered to a patient. Preferably, as used herein, the term "pharmaceutically acceptable" means approved by a regulatory agency of the appropriate governmental agency or listed in the U.S. Pharmacopoeia or other generally recognized pharmacopoeia for use in animals, and more particularly in humans.

A "pharmaceutically acceptable excipient" includes an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The term "treating" includes: (1) preventing the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

The term "subject" includes humans and other mammals, such as domestic animals (e.g., dogs and cats).

"Effective amount" means an amount of a combination of the present invention sufficient to result in the desired therapeutic response. The therapeutic response can be any response that a user (e.g., a clinician) will recognize as an effective response to the therapy. It is further within the skill of one of ordinary skill in the art to determine appropriate treatment duration, appropriate doses, and any potential combination treatments, based upon an evaluation of therapeutic response.

The term "salts" can include acid addition salts or addition salts of free bases. Suitable pharmaceutically acceptable salts (for example, of the carboxyl terminus of the amino acid or peptide) include, but are not limited to, metal salts such as sodium potassium and cesium salts; alkaline earth metal salts such as calcium and magnesium salts; organic amine salts such as triethylamine, guanidine and N-substituted guanidine salts, acetamidine and N-substituted acetamidine, pyridine, picoline, ethanolamine, triethanolamine, dicyclohexylamine, and N,N'-dibenzylethylenediamine salts. Pharmaceutically acceptable salts (of basic nitrogen centers) include, but are not limited to inorganic acid salts such as the hydrochloride, hydrobromide, sulfate, phosphate; organic acid salts such as trifluoroacetate and maleate salts; sulfonates such as methanesulfonate, ethanesulfonate, benzenesulfonate, p-toluenesulfonate, camphor sulfonate and naphthalenesulfonate; and amino acid salts such as arginate, gluconate, galacturonate, alaninate, asparginate and glutamate salts (see, for example, Berge, et al. "Pharmaceutical Salts," *J. Pharma. Sci.* 1977; 66:1).

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Other examples of isotopes suitable for inclusion in the compounds of the invention include isotopes of boron, such as $^{11}$B and $^{10}$B.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Uses and Methods of the Invention

The combinations encompassed by the present invention may be administered in conjunction with other therapies and/or in further combination with other complementary active agents. In such combination therapies, the combinations encompassed by the present invention may be administered prior to, concurrent with, or subsequent to the other therapy and/or active agent. The combinations of the invention and other active agent(s) may also be incorporated into a single dosage form.

The combinations encompassed by the present invention may be applied as a sole therapy or may involve, in addition to the combinations of the invention, conventional surgery or radiotherapy or chemotherapy. Such chemotherapy may include one or more of the following categories of antitumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), A-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, ppl 1-29); such inhibitors also include tyrosine kinase inhibitors, for example inhibitors of the epidermal growth factor family (for example EGFR family tyrosine kinase inhibitors such as A/-(3-chloro-4-fluorophenyl)-7-methoxy-6-(3-morpholinopropoxy)quinazolin-4-amine (gefitinib, ZD1839), A/-(3-ethynylphenyl)-6,7-bis(2-methoxyethoxy)quinazolin-4-amine (erlotinib, OSI-774) and 6-acrylamido-*N*-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R1 15777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1 R kinase inhibitors, IGF receptor (insulin-like growth factor) kinase inhibitors; aurora kinase inhibitors (for example AZD1 152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(xi) immunomodulatory agents (IMiDs), including for example thalidomide, lenalidomide or pomalidomide;

(xii) steroid, including for example dexamethasone or prednisone;

(xiii) histone deacetylase (HDAC) inhibitors, including for example panobinostat or vorinostat; and (xiv) monoclonal antibodies, including for example daratumumab or elotuzumab.

Such combination products employ the combination of this invention within the dosage range described hereinbefore and the other pharmaceutically-active agent within its approved dosage range.

According to this aspect of the invention there is provided a combination suitable for use in the treatment of a cancer (for example a cancer involving a solid tumour or leukaemia) comprising a combination of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour or leukaemia) comprising a combination of the invention as defined hereinbefore, or a pharmaceutically acceptable salt or solvate thereof, and any one of the anti-tumour agents listed under (i)-(xiv) above.

In a further aspect of the invention there is provided a combination of the invention or a pharmaceutically acceptable salt or solvate thereof, in combination with an anti-tumour agent selected from one listed under (i)-(xiv) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a combination of the invention, or a pharmaceutically acceptable salt or solvate thereof in combination with an anti-tumour agent selected from one listed under (i)-(xiv) herein above, in association with a pharmaceutically acceptable diluent or carrier.

Salts, Solvates, and Derivatives of the Combinations of the Invention

The combinations, compositions and methods of the present invention further encompass the use of salts and solvates of the components of the combinations described herein. In one embodiment, the invention disclosed herein is meant to encompass all pharmaceutically acceptable salts of the components of the combinations (including those of any carboxyl terminus of an amino acid as well as those of any basic nitrogen).

Typically, a pharmaceutically acceptable salt of a component of the combinations of the present invention is prepared by reaction of that component with a desired acid or base, as appropriate. The salt may precipitate from solution and be collected by filtration or may be recovered by evaporation of the solvent. For example, an aqueous solution of an acid such as hydrochloric acid may be added to an aqueous suspension of the components and the resulting mixture evaporated to dryness (lyophilized) to obtain the acid addition salt as a solid. Alternatively, the component may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the components of the combination of the invention may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of the acidic compounds are prepared by contacting the free acid form with a sufficient amount of the desired base to produce the salt in the conventional manner. The free acid form may be regenerated by contacting the salt form with an acid and isolating the free acid.

Compounds useful in the practice of the present invention may have both a basic and an acidic centre and may therefore be in the form of zwitterions.

Those skilled in the art of organic chemistry will appreciate that many organic compounds can form complexes, i.e., solvates, with solvents in which they are reacted or from which they are precipitated or crystallized, e.g., hydrates with water. The salts of compounds useful in the present invention may form solvates such as hydrates useful therein. Techniques for the preparation of solvates are well known in the art (see, e.g., Brittain (1999). *Polymorphism in Pharmaceutical solids*. Marcel Decker, New York). The compounds useful in the practice of the present invention can have one or more chiral centers and, depending on the nature of individual substituents, they can also have geometrical isomers.

Pharmaceutical Compositions of the Invention

While it is possible that, for use in the methods of the invention, the combination of the present invention (or each component of the combination of the present invention) may be administered as the bulk substance(s), it is preferable to present each active ingredient in a pharmaceutical formulation, e.g., wherein each agent is in admixture with a pharmaceutically acceptable carrier selected with regard to the intended route of administration and standard pharmaceutical practice.

In one embodiment, there is provided a composition of the combination of the present invention (i.e. a composition comprising both: (i) a proteasome inhibitor selected from the group consisting of: bortezomib, delanzomib, ixazomib, carfilzomib, oprozomib, MG132 and marizomib, and pharmaceutically acceptable salts thereof; and (ii) a cyclic peptide, wherein the cyclic peptide comprises an exposed Arg-Gly-Asp (RGD) moiety).

In one embodiment, compositions of the present invention are presented in unit dosage form.

In an alternative embodiment, there is provided a kit comprising a composition comprising one component of the combination of present invention (i.e. a composition comprising one of (i) a proteasome inhibitor selected from the group consisting of: bortezomib, delanzomib, ixazomib, carfilzomib, oprozomib, MG132 and marizomib), and pharmaceutically acceptable salts thereof; and (ii) a cyclic peptide, wherein the cyclic peptide comprises an exposed Arg-Gly-Asp (RGD) moiety) and a composition comprising the other component of the combination of the present invention (i.e. a composition comprising the other of (i) a proteasome inhibitor selected from the group consisting of: bortezomib, delanzomib, ixazomib, carfilzomib, oprozomib, MG132 and marizomib, and pharmaceutically acceptable salts thereof; and (ii) a cyclic peptide, wherein the cyclic peptide comprises an exposed Arg-Gly-Asp (RGD) moiety).

The composition comprises at least one component of the combination of the invention, and at least one pharmaceutically acceptable excipient or carrier. Preferably the at least one component of the combination of the invention is present in the composition in a therapeutically effective amount.

The compositions of the invention may be immediate-release dosage forms, i.e., dosage forms that release the combination (or each component of the combination) at the site of absorption immediately, or controlled-release dosage forms, i.e., dosage forms that release the combination (or each component of the combination) over a predetermined period of time. Controlled release dosage forms may be of any conventional type, e.g., in the form of reservoir or matrix-type diffusion-controlled dosage forms; matrix, encapsulated or enteric-coated dissolution-controlled dosage forms; or osmotic dosage forms. Dosage forms of such types are disclosed, e.g., in Remington, The Science and Practice of Pharmacy, 20$^{th}$ Edition, 2000, pp. 858-914.

The compositions of the present invention can be administered from one to six times daily, depending on the dosage form and dosage. In an embodiment, it is desirable to administer the cyclic peptide portion of the combination of the present invention daily. For example, the combination of the present invention may involve daily administration of cilengitide. In an embodiment, it is desirable to administer the proteasome inhibitor portion of the combination of the invention weekly or bi-weekly.

The combination employed in the present invention may itself be used in combination with other therapies and/or active agents. Accordingly, the present invention provides, in another embodiment, a pharmaceutical composition as described above useful in the practice of the present invention, or a pharmaceutically acceptable salt or solvate thereof, a further active agent, and, optionally a pharmaceutically acceptable carrier or excipient.

When combined in the same formulation, it will be appreciated that the two components of the combination of the invention are preferably stable in the presence of, and compatible with each other and the other components of the formulation. When formulated separately, they may be provided in any convenient formulation, conveniently in such manner as are known for such compounds in the art.

The combinations (or each component of the combination) presented herein may be formulated for administration in any convenient way for use in human or veterinary medicine. The invention therefore includes pharmaceutical compositions comprising a combination of the invention (or each component of the combination) adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilising agent(s).

The proteasome inhibitor may be administered orally, intravenously or subcutaneously. The cyclic peptide may be administered intravenously or subcutaneously.

Preservatives, stabilizers, dyes and even flavouring agents may be provided in the pharmaceutical composition. Examples of preservatives include sodium benzoate, ascorbic acid and esters of p-hydroxybenzoic acid. Antioxidants and suspending agents may also be used.

The combinations of the present invention (or each component of the combination of the invention) may be milled using known milling procedures such as wet milling to obtain a particle size appropriate for tablet formation and for other formulation types. Finely divided (nanoparticulate) preparations of the compounds may be prepared by processes known in the art, see, e.g., International Patent Application No. WO 02/00196 (SmithKline Beecham).

Suitable examples of pharmaceutically acceptable buffers useful herein include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants useful herein include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetriacetic acid (EDTA), thiourea, tocopherol and butyl hydroxyan The pharmaceutical compositions of the invention may contain from 0.01 to 99% weight per volume of the combinations encompassed by the present invention (or each component of the combinations of the invention).

Dosages

Appropriate patients to be treated according to the methods of the invention include any human or animal in need of such treatment. Methods for the diagnosis and clinical evaluation of the disease condition including its severity in an animal or human will be well known in the art. Thus, it is within the skill of the ordinary practitioner in the art (e.g., a medical doctor or veterinarian) to determine if a patient is in need of treatment. The patient is preferably a mammal, more preferably a human, but can be any subject or animal, including a laboratory animal in the context of a clinical trial, screening, or activity experiment employing an animal model. Thus, as can be readily appreciated by one of ordinary skill in the art, the methods and compositions of the present invention are particularly suited to administration to any animal or subject, particularly a mammal, and including, but not limited to, domestic animals, such as feline or canine subjects, farm animals, such as but not limited to bovine, equine, caprine, ovine, and porcine subjects, research animals, such as mice, rats, rabbits, goats, sheep, pigs, dogs, cats, etc., avian species, such as chickens, turkeys, songbirds, etc.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending on the severity of the condition to be treated, a suitable therapeutically effective and safe dosage, as may readily be determined within the skill of the art, can be administered to subjects. For oral administration to humans, the daily dosage level of the composition may be in single or divided doses. The duration of treatment may be determined by one of ordinary skill in the art, and should reflect the nature of the condition and/or the rate and degree of therapeutic response to the treatment. Typically, a physician will determine the actual dosage which will be most suitable for an individual subject.

The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

In the methods of treatment, the combinations encompassed by the present invention may themselves be administered in conjunction with other therapies and/or in combination with other active agents. For example, the combinations encompassed by the present invention may be administered to a patient in combination with other active agents used to treat that condition. An active agent to be administered in combination with the combinations encompassed by the present invention. In such combination therapies, the combinations encompassed by the present invention may be administered prior to, concurrent with, or subsequent to the other therapy and/or active agent.

Where the combinations encompassed by the present invention are administered in conjunction with another active agent, the individual components of such combinations may be administered either sequentially or simultaneously in separate or combined pharmaceutical formulations by any convenient route. When administration is sequential, either the combinations encompassed by the present invention or the second active agent may be administered first. For example, in the case of a combination therapy with another active agent, the combinations encompassed by the present invention may be administered in a sequential manner in a regimen that will provide beneficial effects of the drug combination. When administration is simultaneous, the combination may be administered either in the same or different pharmaceutical composition. For example, a combinations encompassed by the present invention and another active agent may be administered in a substantially simultaneous manner, such as in a single capsule or tablet having a fixed ratio of these agents, or in multiple separate dosage forms for each agent.

When the combinations of the present invention are used in combination with another agent active in the methods for treating that condition, the dose of each compound may differ from that when the compound is used alone. Appropriate doses will be readily appreciated by those of ordinary skill in the art.

EXAMPLES

The present invention is further illustrated by reference to the following Examples. However, it should be noted that these Examples, like the embodiments described above, are illustrative and are not to be construed as restricting the enabled scope of the invention in any way.

Example 1—Synergistic Effect Exhibited when Bortezomib and a Cyclic RGD Peptide are Combined Relative to the Sum of the Individual Effects of these Components Null hypothesis: 10 µM BTZ combined with 10 µM RGDfC (Arginine-Glycine-Aspartic Acid-D-Phenylalanine-Cysteine) peptide is no more toxic to HEK293 cells than BTZ only.

Method

Established methodology was used to prepare 80-100% confluent monolayers of HEK293 cells in T75 flasks. Cells were cultured in DMEM (Lonza) supplemented with 10% FBS (Gibco), 2 mM L-glutamine, 100 U/mL penicillin and 100 µg/mL streptomycin ("complete DMEM").

The cells in T75 flasks were trypsinised and resuspended in complete DMEM. The cells were counted using a Neubauer chamber and seeded at approximate density of $3 \times 10^4$ cells/cm$^2$ and 7500 cells/cm$^2$ in 96 well flat bottomed tissue culture plates (Corning) 0.1 mL cell suspension per well. Cells were incubated for 24 hours at 37° C./5% $CO_2$ (humidified).

Bortezomib (Fluorochem) was prepared to 30 mM in DMSO and stored below −70° C. until required. To provide a working stock, BTZ was diluted to 10 mM in DMSO.

Peptide stock was prepared by dissolving lyophilised peptide (Anaspec Inc., Fremont Calif., product 63785-1) to 1 mg/mL in phosphate buffered saline pH 7.5 (PBS). Aliquots were stored below −70° C., thawed and diluted in PBS to a working concentration of 500 µM.

One volume BTZ was combined with 479 volumes complete DMEM and 20 volumes of 500 µM peptide (or PBS for negative controls). This resulted in a mixture of BTZ:peptide at approximately equimolar amounts (20 µM).

Control mixtures were prepared in a similar way except using PBS in place of peptide stock and/or DMSO in place of BTZ.

Three 0.1 mL aliquots were added to three wells per plate of each mixture (BTZ+peptide and BTZ+PBS, DMSO+peptide, DMSO+PBS 'diluent only') at each of the cell seeding densities used.

Before addition of BTZ-peptide/PBS mixtures, one plate containing cells at each seeding density used was analysed by Sulforhodamine B staining by a method adapted from Skehan et al. (J. Nat. Cancer Inst. 1990, 82: 1107-1112) in order to establish cell density at time=zero. Briefly: medium was removed from wells and replaced with an equal volume of PBS. One quarter volume of 50% trichloroacetic acid was added gently and the plates incubated at 4° C. for 1-3 hours. Wells were washed 4 times with tap water and allowed to air dry. Sulforhodamine B (Sigma Aldrich, 0.4% w/v in 1% v/v acetic acid) was added to each well and incubated for 15-30 minutes. Wells were washed 4 times with 1% v/v acetic acid and allowed to air-dry. Stain was solubilised by adding 10 mM unbuffered Tris base solution (0.1 mL/well). Optical density ($OD_{570nm}$) was determined using an ELISA plate reader (Dynex MRX, Dynex Technologies).

In total, 5 replicates of the experiment were carried out. Cells treated with peptide/BTZ mixtures or control mixtures were incubated for 24 hours at 37° C./5% $CO_2$ (humidified) then analysed by sulforhodamine B assay.

Data analysis was carried out according to the method of the National Cancer Institute given in <http://web.archive.org/web/20150414025026/http://www.dtp.nci.nih.gov/branches/btb/ivclsp.html>. The average of the background measurements (i.e. no cells, medium only) was subtracted from each reading. '$T_i$' is $OD_{570nm}$ following 24 hours treatment with drugs. $T_z$ is the average of $OD_{570nm}$ at time=0 (minus background). 'C' is the average of the $OD_{570nm}$ given by control wells treated with PBS/DMSO (no peptide or BTZ).

% relative cell growth was given by the equations:

$[(T_i-T_z)/(C-T_z)] \times 100$ (for results where $T_i \geq T_z$)

$[(T_i-T_z)/(T_z)] \times 100$ (for results where Ti<Tz)

Using these equations, control cell growth is assigned a relative cell growth value of 100% and all cell growth values are calculated relative to this figure. Negative values are returned when the OD at time=zero is greater than OD after drug incubation.

A Student's T-test was carried out to determine if there was evidence to reject the null hypothesis (see above). The final relative cell growth values returned from the five experimental replicates was used in a two tailed T-test, paired by experimental replicate, returning a P-value. P-values less than 0.05 are considered sufficient in order to reject the null hypothesis.

Results

A histogram showing mean percentage cell growth in the presence of BTZ or BTZ+peptide is presented in FIG. 1. Results of a Student's T-test returned a P-value of 0.0042 meaning that in this case rejection of the null hypothesis is valid.

Conclusions

The results presented in FIG. 1 clearly illustrate the % relative cell growth values compared to untreated HEK293 cells when treated with 10 µM BTZ, 10 µM BTZ combined with 10 µM RGDfC (Arginine-Glycine-Aspartic Acid-D-Phenylalanine-Cysteine) peptide or 10 µM RGDfC (Arginine-Glycine-Aspartic Acid-D-Phenylalanine-Cysteine) peptide without BTZ. This figure illustrates that peptide combined with BTZ is more toxic at 10 µM concentration than BTZ without peptide or peptide without BTZ.

Example 2—Effect or Cyclic Peptide (Arginine-Glycine-Aspartic Acid-D-Phenylalanine-Lysine)+Proteasome Inhibitor on $\alpha_v\beta_3$ Integrin Positive Cells Vs $\alpha_v\beta_3$ Integrin Negative Cells Summary:

In HEK293 cells (likely to be $\alpha_v\beta_3$ integrin positive, Stoneham C A et al. Clathrin-mediated endocytosis and subsequent endo-lysosomal trafficking of Adeno-associated virus/phage. J. Biol. Chemistry 2012 287(43) 35849-35859. Przystal J M et al. Proteasome inhibition in cancer is associated with enhanced tumor targeting by the adeno-associated virus/phage. Molecular Oncology 2013, 7(1); 55-66), peptide+proteasome inhibitor resulted in increased inhibition/killing versus peptide alone or proteasome inhibitor alone for each of the proteasome inhibitors tested. See FIG. 2 for the results.

This analysis was carried out in the same way as Example 1 using the specified proteasome inhibitors in place of BTZ. Ixazomib (MLN2238) was sourced from Stratech Scientific Ltd. (Oaks Drive, Newmarket, Suffolk). Delanzomib (CEP-18770) was obtained from Source Bioscience (Orchard Place, Nottingham). Carfilzomib and Oprozomib were purchased from Cambridge Bioscience. MG132 (Z-Leu-Leu-al)

was purchased from Sigma-Aldrich. All inhibitors were dissolved in DMSO and used at a final concentration of 10 µM.

In parallel, mixtures were assessed for toxicity against Cos7 cells which reportedly express cancer-associated integrins at extremely low levels (Xu et al., Scientific Reports 2013 3: 2679; Neff S et al. High-Efficiency Utilization of the Bovine Integrin $\alpha_v\beta_3$ as a Receptor for Foot-and-Mouth Disease Virus Is Dependent on the Bovine 133 Subunit. J Virol. 2000 August; 74(16): 7298-7306). Cos7 cells were treated in the same way as the HEK293 cells except Cos7 cells were seeded at densities of $1.2\times10^4$ cells/cm$^2$ and 3000 cells/cm$^2$. In HEK 293 cells, the presence of the RGD peptide significantly increased levels of cell killing compared to the peptide alone, whereas in Cos7 cells, the RGD peptide had no appreciable effect on toxicity. This suggests that the synergistic effect between the RGD cyclic peptide and the proteasome inhibitor is specific to cells that express cancer-associated integrins at higher levels and does not work on every cell type.

Figure 2:
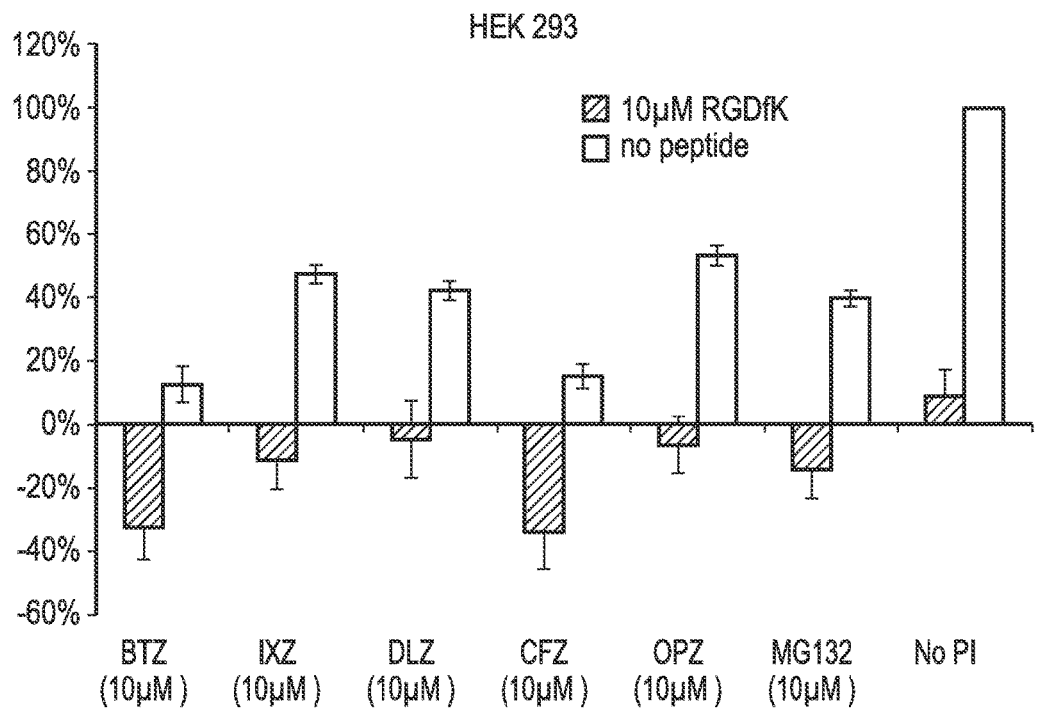
FIG. 2: Enhancement of various proteasome inhibitors by lysine-containing cyclic RGD peptide. Growth relative to control (i.e. negative values represent cell killing, positive values<100% represent cell growth inhibition). Initial single dose assessment (±10 μM each proteasome inhibitor, ±10 μM c(RGDfK) (Arginine-Glycine-Aspartic Acid-D-Phenylalanine-Lysine)) in HEK 293 and Cos7 cells. (BTZ—Bortezomib; IXZ—Ixazomib; DLZ—Delanzomib; CFZ—Carfilzomib; OPZ—Oprozomib; MG132).
Figure 2:
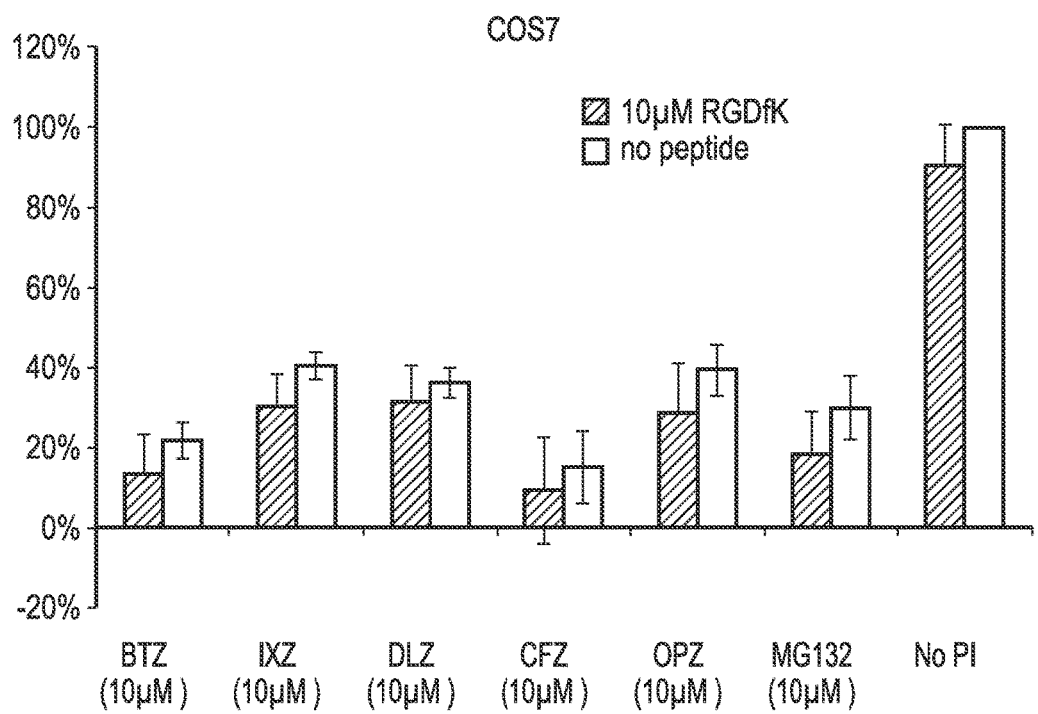

Detailed Description:

Cell lines HEK293 ($\alpha_v\beta_3$ +ve) or COS-7 ($\alpha_v\beta_3$ -ve) were treated with various proteasome inhibitors at a 10 µM concentration±10 µM cyclic peptide cRGDfK (Arginine-Glycine-Aspartic Acid-D-Phenylalanine-Lysine). Growth relative to untreated control cells (normalised to 100%) is shown in FIG. 2. Three independent experiments were performed and values shown are standard error of the mean. Positive values<100% represents cell growth inhibition, while negative values represent cell killing (-100% indicates total cell death). BTZ—Bortezomib; IXZ—Ixazomib; DLZ—Delanzomib; CFZ—Carfilzomib; OPZ—Oprozomib; MG132).

It can be seen that a 10 µM concentration of each proteasome inhibitor causes inhibition of cell growth compared to untreated control cells. This inhibitory effect is approximately the same for each individual proteasome inhibitor in both $\alpha_v\beta_3$ -ve cells (COS-7) and $\alpha_v\beta_3$ +ve cells (HEK293). It is also clear that at a 10 µM concentration some proteasome inhibitors are more active than others irrespective of the $\alpha_v\beta_3$ status of the cells and whether cRGDfK is present or not (carfilzomib and bortezomib show greater activity than ixazomib, delanzomib and oprozomib in both cell types in the absence of cRGDfK).

Compared to untreated control cells, a 10 µM concentration of each proteasome inhibitor on its own causes a delay in cell growth rather than cell death. In contrast, when the cyclic RGD peptide cRGDfK is also added at a 10 µM concentration, a markedly greater cytotoxic effect is seen in $\alpha_v\beta_3$ +ve cells (HEK 293) but not in $\alpha_v\beta_3$ -ve cells (COS-7). Rather than simply delaying cell growth, the proteasome inhibitor now results in cell death. The amount of cell death is dependent upon the specific proteasome inhibitor, but it ranges from 18% cell death (MG132+RGDfK in $\alpha_v\beta_3$ +ve cells (HEK293)) up to as much as 30% or more cell death with carfilzomib or bortezomib+RGDfK in $\alpha_v\beta_3$ +ve cells.

This enhancement was not seen in $\alpha_v\beta_3$ -ve cells (COS-7) indicating that it is a specific effect of adding an RGD peptide to cells expressing $\alpha_v\beta_3$ integrins.

Example 3—Synergistic Effect Exhibited when (i) Bortezomib or Carfilzomib; and (ii) Cilengitide Peptide are Combined Relative to the Sum of the Individual Effects of these Components Null hypothesis: 10 µM BTZ or 10 µM CFZ combined with 1 µM or 10 µM cilengitide peptide is no more toxic to HEK293 cells than BTZ or CFZ only.

Method

HEK293 cells were seeded in 96 well plates as per paragraph [0124] and treated with proteasome inhibitors (PI) Bortezomib (BTZ) or Carfilzomib (CFZ) (10 µM)±Cilengitide (1 µM or 10 µM) for 24 hours as per Example 2.

Cilengitide was obtained from Bioquote Ltd. (product code A8660) and prepared to 500 µM in PBS (pH 7.5) before addition to medium to achieve the desired final concentration. Five replicates of the experiment were carried out (the lower concentration of cilengitide was only included for 4 of the experimental replicates). Note that data shown is from the lower cell seeding density (7500 cells/cm$^2$).

Results

Figure 3:
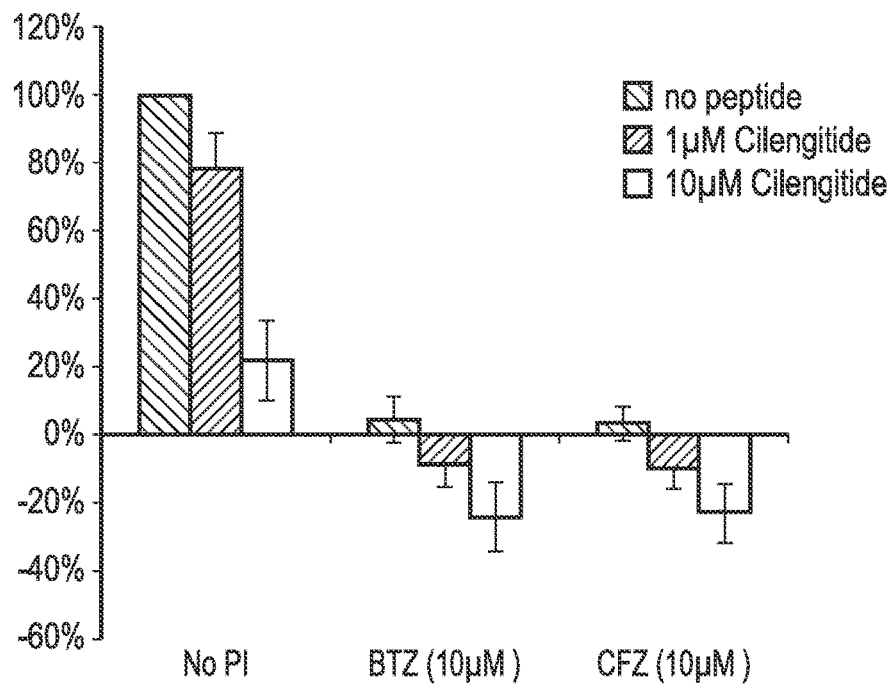
FIG. 3: Enhancement of bortezomib and carfilzomib proteasome inhibitors by cilengitide. Growth relative to control (i.e. negative values represent cell killing, positive values<100% represent cell growth inhibition). Initial single dose assessment (±10 μM bortezomib or carfilzomib, ±1 or 10 μM cilengitide in HEK 293. (BTZ—Bortezomib; CFZ—Carfilzomib).

A histogram showing mean percentage cell growth in the presence of BTZ, CFZ, BTZ+cilengitide peptide or CFZ+cilengitide is presented in FIG. 3.

Growth relative to untreated control cells (normalised to 100%) is shown in FIG. 3. Three independent experiments were performed and values shown are the standard error of the mean. Positive values<100% represents cell growth inhibition, while negative values represent cell killing (-100% indicates total cell death).

Conclusions

The results presented in FIG. 3 clearly illustrate the % relative cell growth values compared to untreated HEK293 cells when treated with 10 µM BTZ, 10 µM BTZ combined with 1 µM cilengitide peptide, 10 µM BTZ combined with 10 µM cilengitide peptide, 10 µM CFZ, 10 µM CFZ combined with 1 µM cilengitide peptide, 10 µM CFZ combined with 10 µM cilengitide peptide, 1 µM cilengitide peptide without BTZ or CFZ, 10 µM cilengitide peptide without BTZ or CFZ and no cilengitide and no BTZ or CFZ. This figure illustrates that peptide combined with BTZ or CFZ is more toxic than BTZ or CFZ without peptide or peptide without BTZ or CFZ.

Example 4: Effect of Cilengitide and BTZ on T47D Breast Cancer Cell Line

T47D cells were cultured exactly as HEK293 and Cos7 cells (Example 1). For assessment of combined BTZ and cilengitide toxicity, T47D cells were seeded at a density of 7500 cells/cm$^2$ in 96-well cell culture plates and incubated for 24 hours. Cilengitide was diluted to 20 µM in complete DMEM, then 3 serial tenfold dilutions of this were performed in complete DMEM (2 µM, 200 nM and 20 nM). Complete DMEM containing no cilengitide was provided for negative controls.

Serial tenfold dilutions of bortezomib were prepared (from 3 mM to 300 nM) in DMSO. These dilutions (or DMSO for wells containing no BTZ) were added to aliquots of complete DMEM containing 0-20 µM cilengitide for a 1/150 dilution. Aliquots (0.1 mL) of each mixture were added to wells already containing 0.1 mL medium (in duplicate), resulting in a matrix of cilengitide (10 nM-10 µM) and/or BTZ (1 nM-10 µM) or neither agent (diluent only).

Plates were incubated for 24 hours then analysed by sulforhodamine B assay as per example 1. OD$_{570nm}$ readings were divided by those resulting from negative control (diluent only) wells and expressed as a percentage. Three independent replicates of this experiment were carried out.

Figure 4:
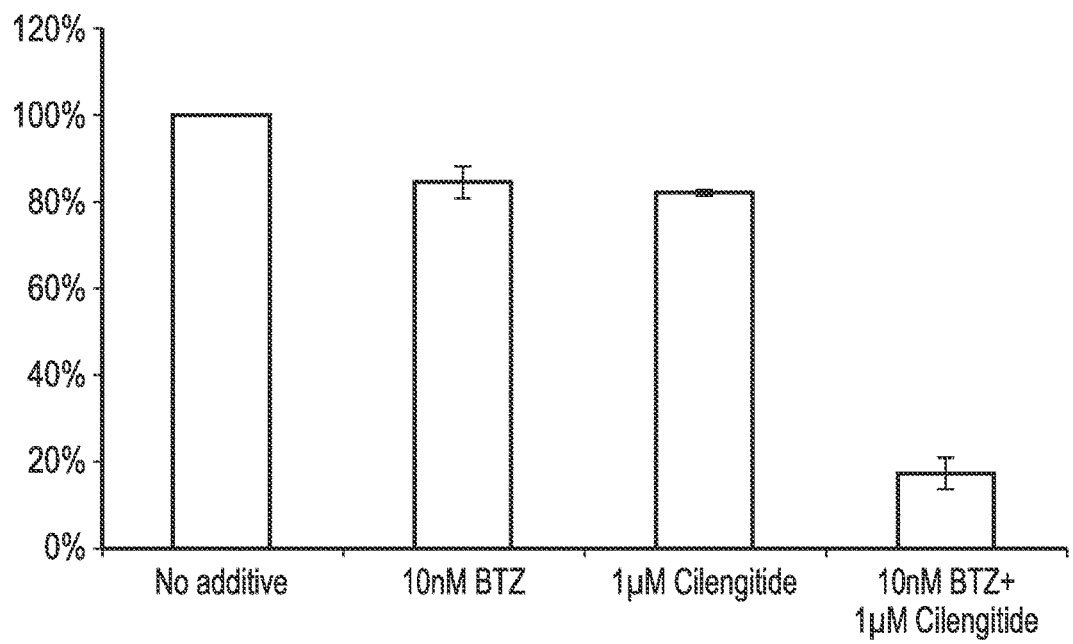
FIG. 4: Effect of Cilengitide and BTZ on T47D breast cancer cell line. Growth of cells relative to control (untreated) cells. Graphs show results of sulforhodamine B assay, plotted as $OD_{570nm}$ (test)/$OD_{570nm}$ (control). Control=wells treated with diluents only (='No additive').

The results are provided in FIG. 4, which shows data obtained using cilengitide (1 μM) and/or bortezomib (10 nM). Viability relative to untreated control cells (normalised to 100%) is shown in FIG. 4.

While T47D breast cancer cells showed only very marginal sensitivity to bortezomib when administered alone at a 10 nM concentration (80% viability compared with the untreated controls), a greatly increased sensitivity was observed when co-administered with 1 μM cilengitide (less than 20% of the viability compared with controls).

Example 5: Determination of In Vitro Synergy (Combination Index) of Bortezomib and Cilengitide in T47D Breast Cells To identify whether the action of both agents in combination was additive or super-additive (i.e. synergistic), pairs of concentrations resulting in 50% reduction in viability were plotted in an isobologram (Tallarida: J Pharmacol Exp Ther. 2001; 298: 865-72), whereby concentrations of each agent are arranged on the x and y axes and a line is drawn between the concentration of each agent resulting in 50% reduction in viability delivered as a single agent (i.e. the $IC_{50}$). The $IC_{50}$ of the single agents were estimated by extrapolation of points representing 50% reduction in viability from line graphs of % viability versus concentration of agent. The isoboles were obtained similarly by extrapolation of points representing 50% reduction in viability from line graphs of % viability versus concentration of one agent at variable concentration with the other agent supplied at a fixed concentration.

Figure 6:
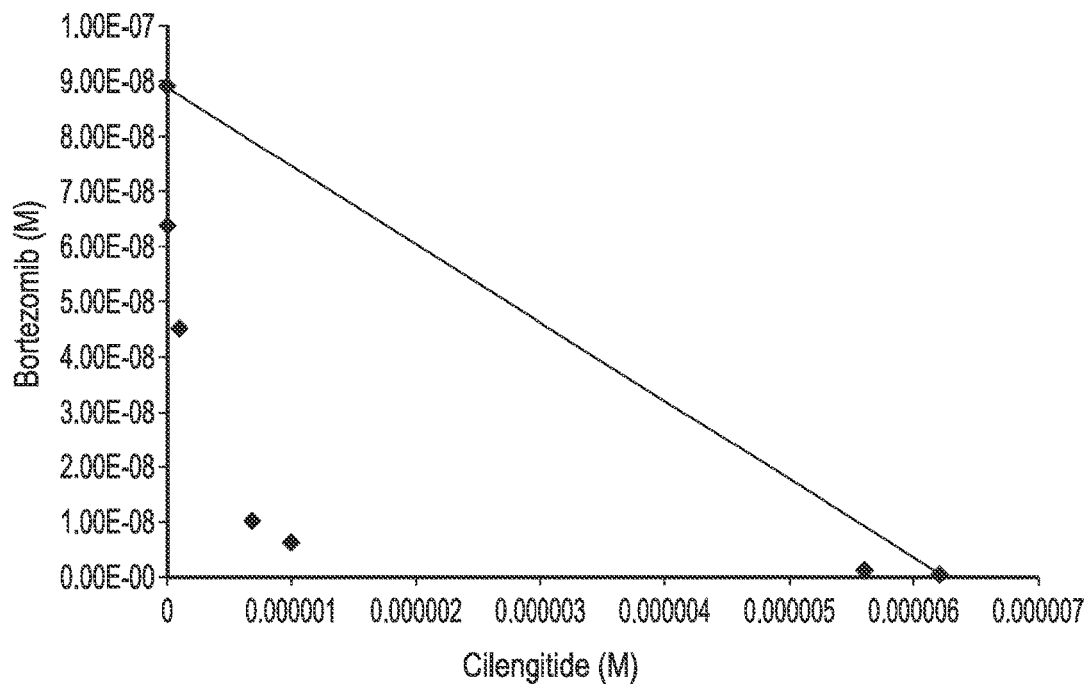
FIG. 6: Isobologram showing bortezomib and cilengitide synergy at various molar ratios. Combinations of both agents which result in a 50% reduction in viability are assessed compared to the expected doses of both agents predicted to show the same reduction in viability if the combined effect was additive. The positions of the dose pairs (isoboles) indicate whether the two agents are additive (falling on or close to the line), sub-additive/antagonistic (falling above/right of the line) or superadditive/synergistic (falling below/left of the line).

The position of the points on this graph (FIG. 6) indicates whether a combined effect is synergistic (falling below/left of the line) antagonistic (falling above/right of this line) or additive (on or close to this line). All points on this isobologram combination indices (CI) were calculated according to the equation given in Zhao et al. (Clin. Cancer Res. 2004; 10:7994-8004) and are presented below in Table 1.

$$CI = \frac{C_{A,x}}{IC_{x,A}} + \frac{C_{B,x}}{IC_{x,B}}$$

$C_{A,x}$ and $C_{B,x}$ are the concentrations of drug A and drug B used in combination to achieve x % drug effect. $IC_{x,A}$ and $IC_{x,B}$ are the concentrations for single agents to achieve the same effect. These indices suggest that the most striking synergy is exhibited when the molar ratio of cilengitide:BTZ is between 70:1 (CI=0.22) and 170:1 (CI=0.23).

TABLE 1

Combination indices (CI) obtained using different ratios of cilengitide:BTZ.
Combination indices <1 indicates synergy,
>1 indicates antagonism and CI = 1 indicates additivism.

| Cilengitide (M) | Bortezomib (M) | CI |
| --- | --- | --- |
| 0 | 8.90e−08 | 1.00 |
| 1.00E−08 | 6.35E−08 | 0.72 |
| 1.00E−07 | 4.50E−08 | 0.52 |
| 6.90E−07 | 1.00E−08 | 0.22 |
| 1.00E−06 | 6.00E−09 | 0.23 |
| 5.60E−06 | 1.00E−09 | 0.91 |
| 6.20e−06 | 0 | 1.00 |

Thus a clear synergistic effect is seen between cilengitide and bortezomib in breast cancer cell line T47D.

Example 6: Effect of BTZ and Cilengitide Combination Therapy on Myeloma Xenografts In Vivo Female (8-12 week old) CB.17 SCID mice were implanted with $1 \times 10^7$ NCI-H929 tumor cells by subcutaneous injection in 50% Matrigel in flank. Tumours were allowed to reach an average size of 90-130 mm$^3$, mice were split into groups N=10 per group, then dosing commenced (Day 1). Animals were dosed i.v. with bortezomib (BTZ) or vehicle (0.9% saline) on Day 1. Cilengitide (45 mg/kg) or vehicle (0.9% saline) was injected i.p. on Days 1, 2 and 3.

Tumour volume is calculated as=[length*(width$^2$)]/2

Figure 5:
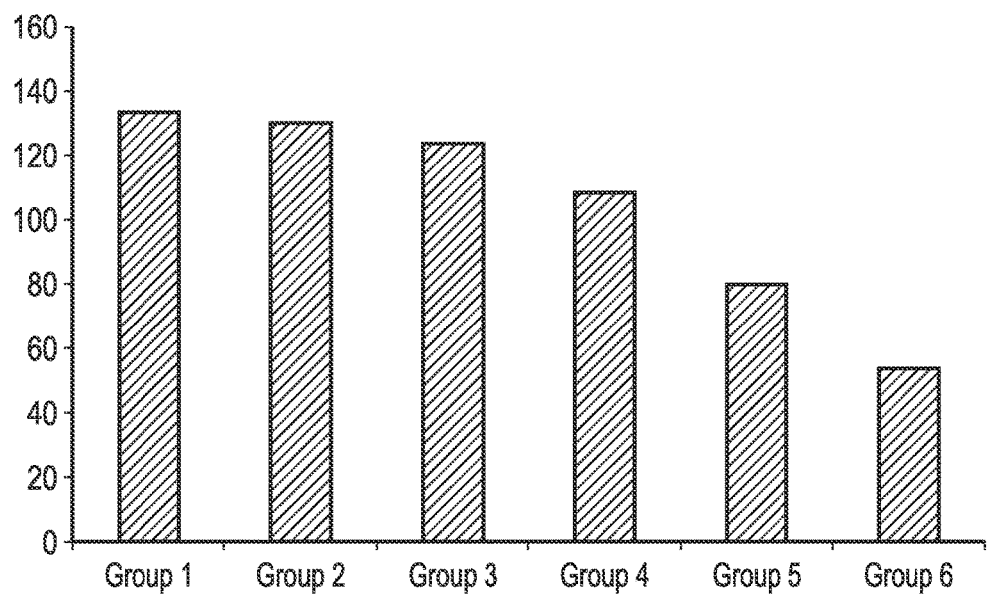
FIG. 5: Effect of BTZ and cilengitide combination therapy on myeloma xenografts in vivo. The mean tumour size for CB.17 SCID mice implanted with $1 \times 10^7$ NCI-H929 tumor cells on day 4 of dosing with: (1) vehicle+vehicle; (2) vehicle+cilengitide (45 mg/kg); (3) 0.2 mg/kg BTZ+vehicle; (4) 0.2 mg/kg BTZ+cilengitide (45 mg/kg); (5) 1 mg/kg BTZ+vehicle; and (6) 1 mg/kg BTZ+cilengitide (45 mg/kg).

The data plotted is the mean tumour size for each group on day 4. Treatment groups were: (1) vehicle+vehicle; (2) vehicle+cilengitide; (3) 0.2 mg/kg BTZ+vehicle; (4) 0.2 mg/kg BTZ+cilengitide; (5) 1 mg/kg BTZ+vehicle; (6) 1 mg/kg BTZ+cilengitide. The results are provided in FIG. 5.

Example 7: In Vivo Sub Cutaneous Tumour Study of Combined Cilengitide and Bortezomib Treatment Against NCI H-929 Multiple Myeloma Cell Line A scoping study was conducted to compare the efficacy of bortezomib with a bortezomib/cilengitide combination regime in vivo in a sub cutaneous SCID mouse xenograft model using NCI H-929 human multiple myeloma cells. The dose of bortezomib tested was 1 mg/kg. H929 cells were implanted and allowed to grow until mean tumour volumes of 101-103 mm$^3$ were reached on Day 1, whereupon treatment began. This was then continued until Day 21.

While most of the mice given 'bortezomib-only' responded well to the drug, with a 90% overall response rate, mice given the bortezomib+cilengitide combination exhibited a marked improvement in several areas (Table 2). Both response rates and speed of responses were enhanced. By Day 4, 30% of bortezomib-only treated mice showed a response; for the combination therapy group the figure was 60%. By Day 8, only 10% of the bortezomib-only treated mice showed a complete response, for the combination therapy group the figure was 50%. All mice given the combination therapy had responded by Day 12, while by the last treatment day (Day 21) one (10%) of the bortezomib-only group had still failed to respond at all.

On Day 21 treatment was stopped and all mice were followed for an additional 3 weeks to monitor the rate and incidence of tumour reappearance. By Day 42 60% of animals remained 'cured' in both groups (i.e. tumours did not regrow during this period). For the remaining 4 animals in each group, outcomes were as follows. For the group treated with only bortezomib, 3 animals showed a complete relapse (i.e. tumours did not show a partial or total response as per the criteria detailed in Table 2), while 1 animal reached end point and was culled (tumour volume>2000 mm$^3$). For the group treated with the combination therapy, 2 animals relapsed, while 2 still exhibited a partial response. No animals reached end point in the combination therapy group.

TABLE 2

Summary for efficacy results of bortezomib and bortezomib + cilengitide in NCI-H929 sub-cutaneous xenograft mouse tumor model at 'high' bortezomib dose

| | | Day of Study (treatment commenced on Day 1) | | | | | | |
|---|---|---|---|---|---|---|---|---|
| | | 1 | 4 | 8 | 12 | 15 | 18 | 21 |
| Bortezomib 1 mg/kg | No response | 10 | 7 | 3 | 2 | 2 | 1 | 1 |
| | Partial response | 0 | 3 | 6 | 4 | 4 | 5 | 4 |
| | Complete response | 0 | 0 | 1 | 4 | 4 | 4 | 5 |
| N = 10 mice per group | Total RR % | 0% | 30% | 70% | 80% | 80% | 90% | 90% |
| Bortezomib 1 mg/kg + cilengitide 45 mg/kg | No response | 10 | 4 | 1 | 0 | 0 | 0 | 0 |
| | Partial response | 0 | 6 | 4 | 5 | 5 | 4 | 2 |
| | Complete response | 0 | 0 | 5 | 5 | 5 | 6 | 8 |
| N = 10 mice per group | Total RR % | 0% | 60% | 90% | 100% | 100% | 100% | 100% |
| Cilengitide 45 mg/kg | No response | 10 | 10 | 10 | 10 | 10 | 10 | 10 |
| | Partial response | 0 | 0 | 0 | 0 | 0 | 0 | 0 |
| | Complete response | 0 | 0 | 0 | 0 | 0 | 0 | 0 |
| N = 10 mice per group | Total RR % | 0% | 0% | 0% | 0% | 0% | 0% | 0% |

Partial response (PR) is defined as the first measurement of the tumor volume being 50% or less of its Day 1 volume for three consecutive measurements during the course of the study, and equal to or greater than 13.5 mm$^3$ for one or more of these three measurements. In a complete response (CR), the tumor volume was less than 13.5 mm$^3$ for three consecutive measurements during the course of the study. Total response rate (RR) is the sum of PR+CR. Treatment began on day 1 and was stopped on Day 21. Bortezomib was given as Velcade (1 mg/kg IV biweekly) with cilengitide (45 mg/kg IP, QD).

In Example 8: In Vivo Sub Cutaneous Tumour Study of Combined Cilengitide and Bortezomib Treatment Against NCI H-929 Multiple Myeloma Cell Line In order to confirm and extend the observations described in Example 7, a similar experiment was conducted, whereby the BTZ dose was varied (0.2, 0.5, 0.7 and 0.9 mg/kg by biweekly intravenous injection). Cilengitide or vehicle was supplied as daily intra-peritoneal injection (45 mg/kg). Tumour growth inhibition (TGI) was assessed at the primary endpoint of the study (either day 21 or the day that vehicle-treated control animals reached a mean tumour volume of 2000 mm$^3$—in this case this endpoint was reached on day 18).

Figure 9:
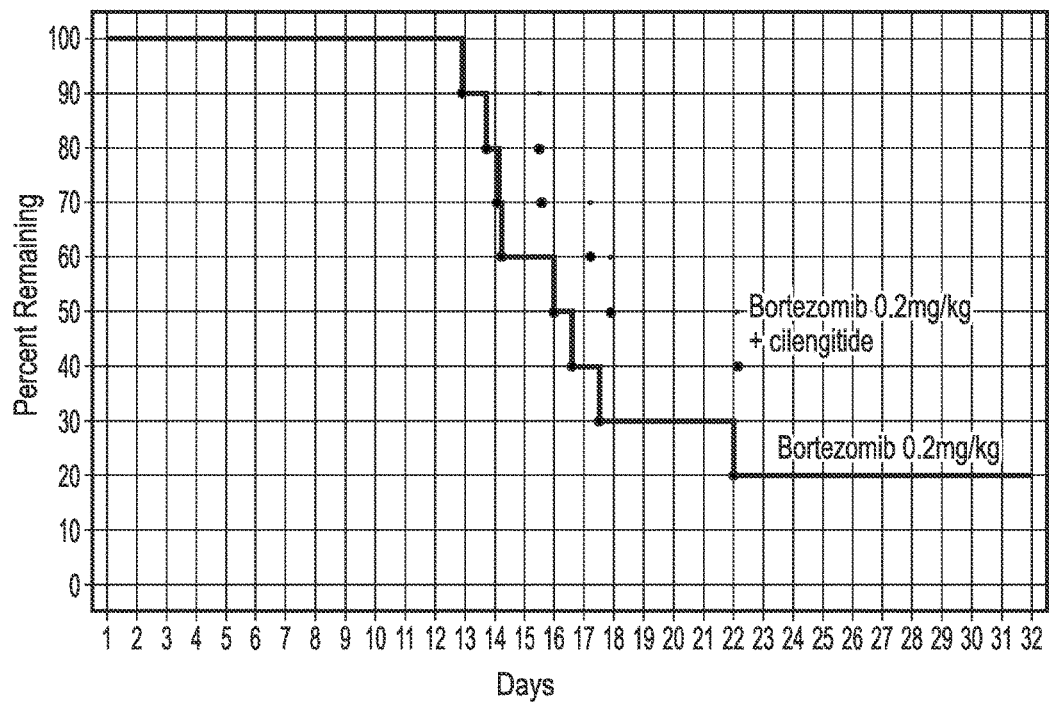
FIG. 9: Kaplan-Meier plot of 0.2 mg/kg BTZ (biweekly intravenous injection)±45 mg/kg cilengitide (daily intra-peritoneal injection) until day 31 providing the difference in time to endpoint (TTE). TTE was calculated as TTE=[log (endpoint volume)-b]/m where TTE is expressed in days, endpoint volume is expressed in mm³, b is the intercept, and m is the slope of the line obtained by linear regression of a log-transformed tumour growth data set.
Figure 10:
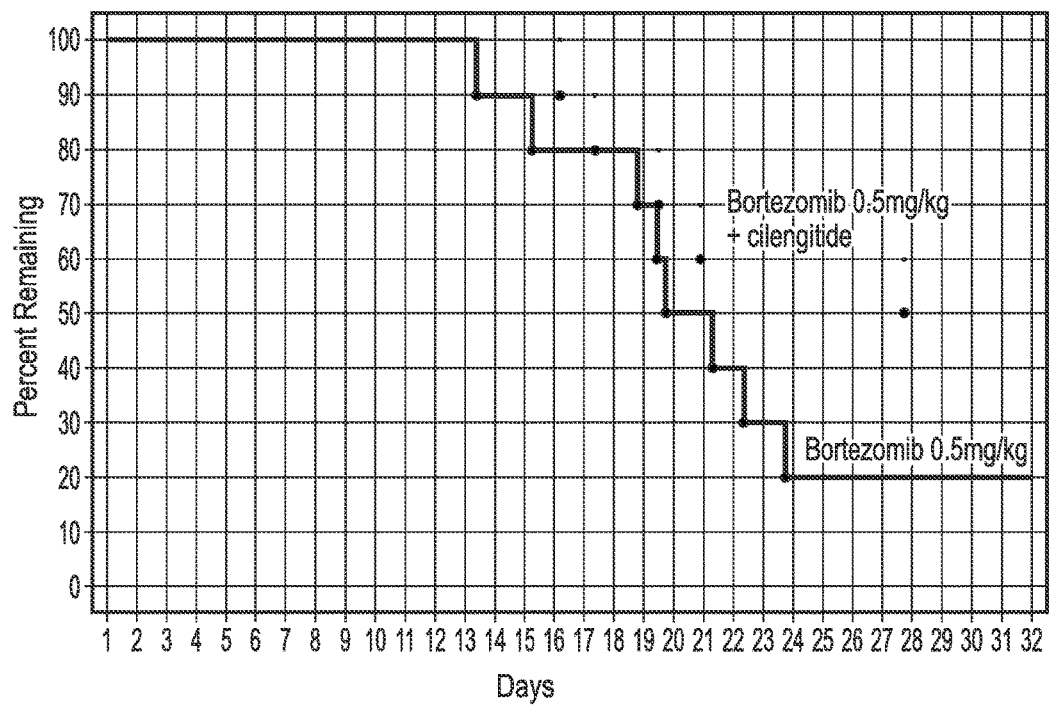
FIG. 10: Kaplan-Meier plot of 0.5 mg/kg BTZ (biweekly intravenous injection)±45 mg/kg cilengitide (daily intra-peritoneal injection) until day 31 providing the difference in time to endpoint (TTE). TTE was calculated as TTE=[log (endpoint volume)-b]/m where TTE is expressed in days, endpoint volume is expressed in mm³, b is the intercept, and m is the slope of the line obtained by linear regression of a log-transformed tumour growth data set.

After this point, dosing was continued in groups receiving 0.2 mg/kg and 0.5 mg/kg BTZ±cilengitide until day 31 to allow comparative tumour growth delay (i.e. difference in time to endpoint (TTE). Endpoint volume was defined as 2000 mm$^3$, and upon reaching or exceeding this volume animals were sacrificed. TTE was calculated as TTE=[log (endpoint volume)-b]/m where TTE is expressed in days, endpoint volume is expressed in mm$^3$, b is the intercept, and m is the slope of the line obtained by linear regression of a log-transformed tumour growth data set. TTE values were plotted in Kaplan-Meier diagrams (FIGS. 9 and 10).

BTZ exhibited a sharp dose-effect curve indicative of its narrow therapeutic window. Doses of 0.7 mg/kg and greater exhibited almost complete TGI, therefore extended dosing to examine TGI was not likely to be informative. Concentrations of 0.5 mg/kg BTZ and below, without cilengitide, were virtually ineffective, leading to no apparent tumour growth inhibition.

Figure 7:
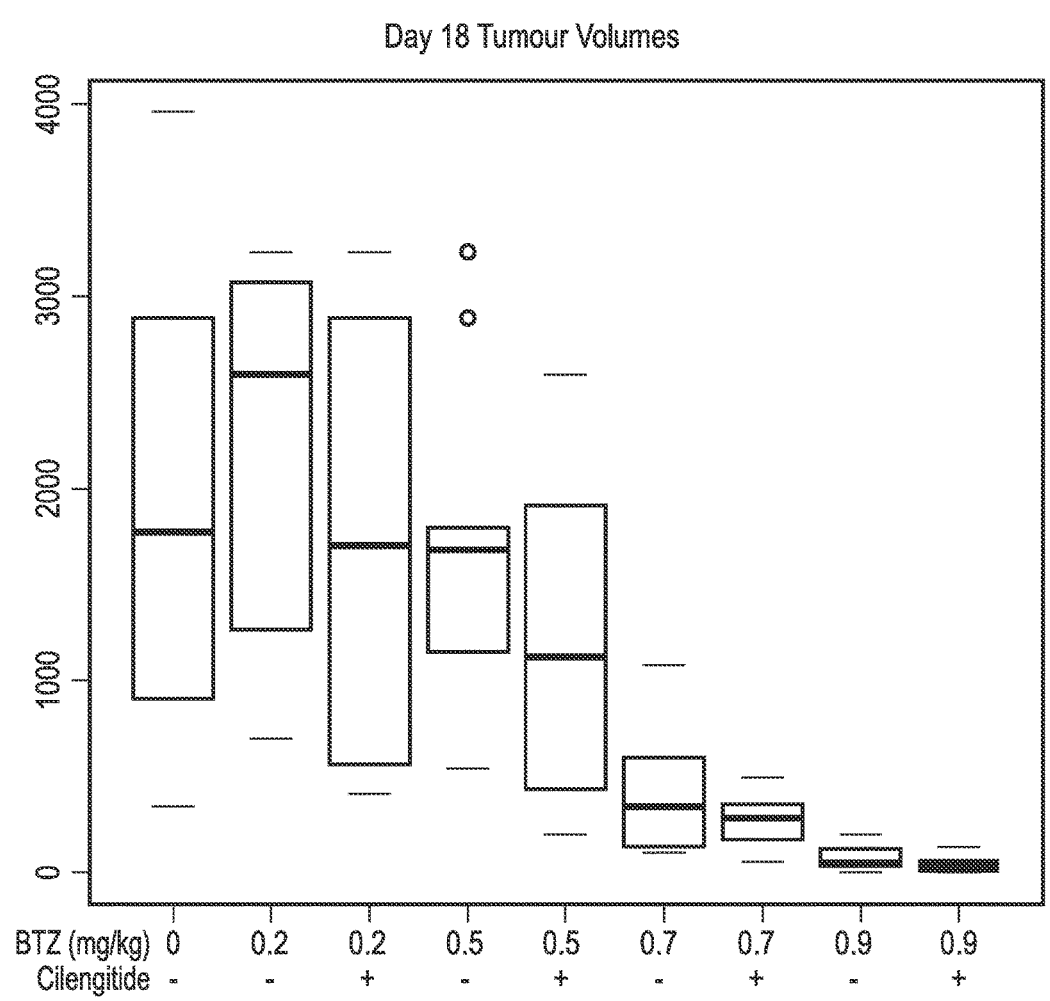
FIG. 7: Effect of BTZ (0.2, 0.5, 0.7 or 0.9 mg/kg by biweekly intravenous injection) and cilengitide or vehicle (45 mg/kg by daily intra-peritoneal injection). Tumour growth inhibition (TGI) was assessed at the primary endpoint of the study (either day 21 or the day that vehicle-treated control animals reached a mean tumour volume of 2000 mm³—in this case this endpoint was reached on day 18).
Figure 8:
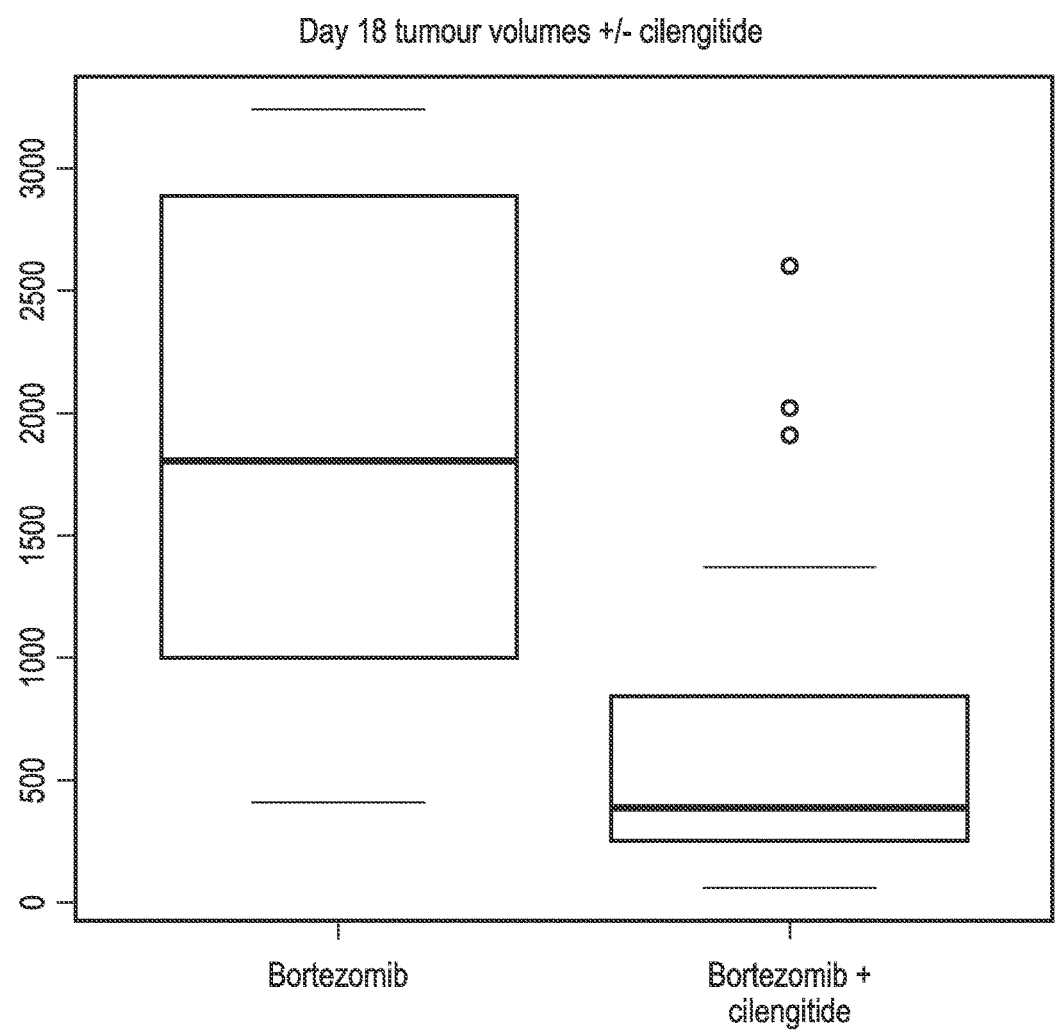
FIG. 8: Effect of BTZ (0.2, 0.5, 0.7 or 0.9 mg/kg by biweekly intravenous injection) and cilengitide or vehicle (45 mg/kg by daily intra-peritoneal injection). Data from all groups in FIG. 7 was combined regardless of bortezomib concentration and treated as two groups, n=40 mice/group (i.e. plus or minus cilengitide). A non-parametric Kruskal-Wallis test was used to assess statistical significance of the difference between the tumour volumes exhibited by these groups ($P=3.465 \times 10^{-7}$).

Individual between group differences in TGI were not statistically significant due to high levels of variability within groups, however a trend toward tumour growth inhibition in the presence of cilengitide was observed (FIG. 7). This trend is more obvious when data from all groups was combined regardless of bortezomib concentration, and treated as two groups, n=40 mice/group (i.e. plus or minus cilengitide). A non-parametric Kruskal-Wallis test was used to assess statistical significance of this finding (P=3.465× $10^{-7}$, FIG. 8). Cilengitide also increased the TTE of animals treated with 0.2 or 0.5 mg/kg BTZ (FIGS. 9 and 10).

What is claimed is:

1. A combination comprising: (i) a proteasome inhibitor or a pharmaceutically acceptable salt thereof; and (ii) a cyclic peptide or a pharmaceutically acceptable salt thereof, wherein the cyclic peptide or a pharmaceutically acceptable salt thereof comprises an exposed Arg-Gly-Asp (RGD) moiety; and wherein the ratio of the proteasome inhibitor or a pharmaceutically acceptable salt thereof to the cyclic peptide or a pharmaceutically acceptable salt thereof ranges from 1:5000 to 1:10 w/w.

2. The combination of claim 1, wherein the proteasome inhibitor is a boronate compound or a pharmaceutically acceptable salt thereof.

3. The combination of claim 2, wherein the boronate compound or a pharmaceutically acceptable salt thereof is selected from the group consisting of: bortezomib, delanzomib and ixazomib, or a pharmaceutically acceptable salt thereof.

4. The combination of claim 1, wherein the proteasome inhibitor is an epoxyketone compound, or a pharmaceutically acceptable salt thereof.

5. The combination of claim 4, wherein the epoxyketone compound or a pharmaceutically acceptable salt thereof is selected from the group consisting of: carfilzomib and oprozomib, or a pharmaceutically acceptable salt thereof.

6. The combination of claim 1, wherein the proteasome inhibitor is a peptide aldehyde compound, or a pharmaceutically acceptable salt thereof.

7. The combination of claim 6, wherein the peptide aldehyde compound or a pharmaceutically acceptable salt thereof is MG132, or a pharmaceutically acceptable salt thereof.

8. The combination of claim 1, wherein the proteasome inhibitor is a β-lactone protease inhibitor compound, or a pharmaceutically acceptable salt thereof.

9. The combination of claim 8, wherein the β-lactone protease inhibitor compound or a pharmaceutically acceptable salt thereof is marizomib, or a pharmaceutically acceptable salt thereof.

10. The combination of claim 1, wherein the cyclic peptide has the structure:

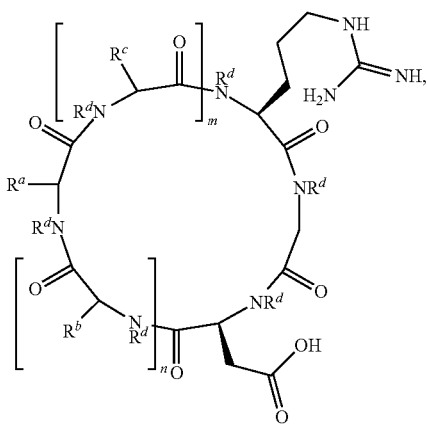

wherein:
$R^a$, $R^b$ and $R^c$ are amino acid side-chains;
$R^d$ are each independently selected from the group consisting of H, $C_1$ alkyl, $C_2$ alkyl and $C_3$ alkyl;
m is 0, 1 or 2;
n is 0, 1 or 2;
provided that the value of n+m is 0, 1 or 2,
or a pharmaceutically acceptable salt thereof.

11. The combination of claim 10, wherein the cyclic peptide has the structure:

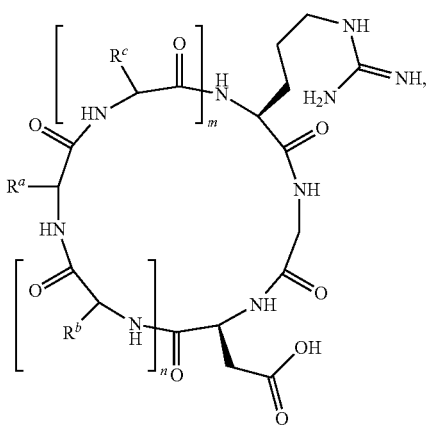

wherein:
$R^a$, $R^b$ and $R^c$ are amino acid side-chains;
m is 0, 1 or 2;
n is 0, 1 or 2;
provided that the value of n+m is 0, 1 or 2,
or a pharmaceutically acceptable salt thereof.

12. The combination of claim 10, wherein $R^a$, $R^b$ and $R^c$ are amino acid side-chains of alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, selenocysteine or pyrrolysine, or a pharmaceutically acceptable salt thereof.

13. The combination of claim 10, wherein m is 0 and n is 0; m is 1 and n is 0; or m is 0 and n is 1.

14. The combination of claim 10, wherein the cyclic peptide has a structure:

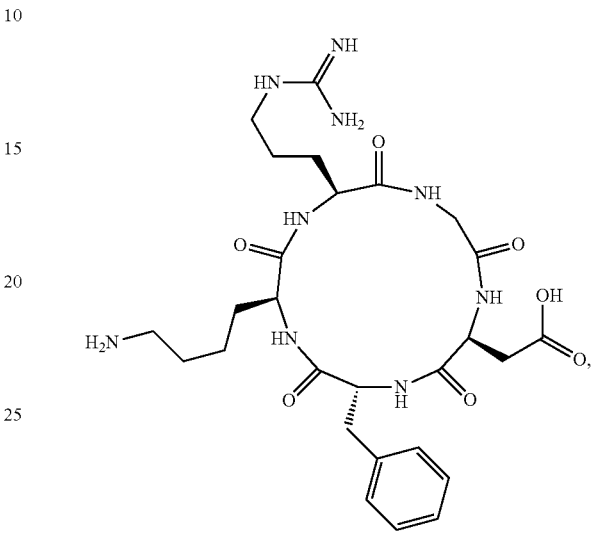

or a pharmaceutically acceptable salt thereof.

15. The combination of claim 10, wherein each amine nitrogen of the amino acid residues of the cyclic peptide is independently mono-alkylated.

16. The combination of claim 10, wherein the cyclic peptide is cilengitide with the structure:

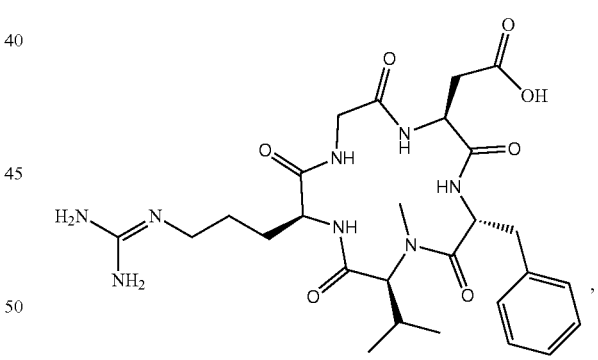

or a pharmaceutically acceptable salt thereof.

17. The combination of claim 1, for use as a medicament.

18. The combination of claim 1, for use in the treatment of a disorder selected from the group consisting of: mantle cell lymphoma, multiple myeloma, breast cancer, glioblastoma, graft-versus-host disease, Smoldering Myeloma and Monoclonal Gammopathy of Unknown Significance (MGUS), or a combination thereof.

19. The combination of claim 18, wherein the disorder is multiple myeloma, and the multiple myeloma is metastatic multiple myeloma.

20. The combination of claim 18, wherein the disorder is breast cancer, and the breast cancer is metastatic breast cancer.

21. The combination of claim 18, wherein the disorder is glioblastoma, and the glioblastoma is glioblastoma multiforme.

22. A pharmaceutical composition comprising the combination of claim 1 and a pharmaceutically acceptable excipient.

23. A kit comprising as separate components: (i) a proteasome inhibitor or a pharmaceutically acceptable salt thereof; and (ii) a cyclic peptide or a pharmaceutically acceptable salt thereof, wherein the cyclic peptide or a pharmaceutically acceptable salt thereof comprises an exposed Arg-Gly-Asp (RGD) moiety.

* * * * *